US007166612B2

(12) United States Patent
Flaumenhaft

(10) Patent No.: US 7,166,612 B2
(45) Date of Patent: Jan. 23, 2007

(54) METHODS FOR REDUCING PLATELET ACTIVATION PLATELET AGGREGATON OR THROMBOSIS

(75) Inventor: Robert Charles Flaumenhaft, Newton, MA (US)

(73) Assignee: Beth Israel Deaconess Medical Center, Boston, MA (US)

( * ) Notice: Subject to any disclaimer, the term of this patent is extended or adjusted under 35 U.S.C. 154(b) by 390 days.

(21) Appl. No.: 10/740,182

(22) Filed: Dec. 18, 2003

(65) Prior Publication Data

US 2004/0147540 A1 Jul. 29, 2004

Related U.S. Application Data

(63) Continuation-in-part of application No. PCT/US02/19843, filed on Jun. 24, 2002.

(60) Provisional application No. 60/300,932, filed on Jun. 26, 2001.

(51) Int. Cl.
*A61K 31/44* (2006.01)
*A61K 31/47* (2006.01)

(52) U.S. Cl. ...................... 514/290; 514/291; 514/311; 514/312; 514/314

(58) Field of Classification Search ................ 514/290, 514/291, 311, 314
See application file for complete search history.

(56) References Cited

U.S. PATENT DOCUMENTS

| | | | | |
|---|---|---|---|---|
| 3,755,332 A | * | 8/1973 | Wasley et al. | 546/160 |
| 4,011,332 A | * | 3/1977 | Westervelt et al. | 118/301 |
| 4,361,563 A | * | 11/1982 | Austel et al. | 514/247 |
| 4,616,018 A | * | 10/1986 | Hauel et al. | 514/252.06 |
| 4,699,909 A | * | 10/1987 | Hauel et al. | 514/252.06 |
| 4,923,869 A | * | 5/1990 | Prucher et al. | 514/252.03 |
| 4,954,499 A | * | 9/1990 | Prucher | 514/247 |
| 4,954,501 A | * | 9/1990 | Herter et al. | 514/252.02 |
| 4,957,920 A | * | 9/1990 | Morsdorf et al. | 514/252.06 |
| 4,968,683 A | * | 11/1990 | Morsdorf et al. | 514/252.02 |
| 5,039,675 A | * | 8/1991 | Morsdorf et al. | 514/252.06 |
| 6,801,405 B2 | * | 10/2004 | Boutaghou et al. | 360/265.9 |
| 6,818,772 B2 | * | 11/2004 | Kym et al. | 546/160 |

OTHER PUBLICATIONS

"WIN 17317-3, a New High-Affinity Probe for Voltage-Gated Sodium Channels", Wanner et al., Biochemistry, 1999, vol. 38, No. 34, pp. 11137-11146.*
Xu et al., Hecheng Huaxue, 1999, abstract, 7(2), pp. 194-197.*
Eggert et al., Archiv der Pharmazie, abstract, 1990, 323(9), pp. 611-618.*
Omburo, et al., "Divalent Metal Cation Requirement and Possible Classification of cGMP-Inhibited Phosphodiesterase as a Metallohydrolase", Archives of Biochemistry and Biophysics (1995), V. 323, pp. 1-5.

Chou, et al., "Mechanism of Inhibition of Platelet Aggregation by HCL-31D", European Journal of Pharmacology (2000), V. 387, pp. 125-131.
Coughlin, "Thrombin Signalling and Protease-Activated Receptors", Nature (2000), V. 407, pp. 258-264.
Offermans, et al., "Defective Platelet Activation in $G\alpha_q$ -Deficient Mice", Nature (1997), V. 389, pp. 183-186.
Palabrica, et al., "Leukocye Accumulation Promoting Fibrin Deposition is Mediated *in vivo* by P-Selectin on Adherent Platelets", Nature (1992), V. 359, pp. 848-851.
Bazzoni, et al., "Platelet-Neutrophil Interactions. Possible Relevance in the Pathogenesis of Thrombosis and Inflammation", Haematologica (1991), V. 76, pp. 491-499.
Kazura, "Platelet-Neutrophil Interaction: Modulation of the Inflammatory Response", Journal of Laboratory and Clinical Medicine (1989), V. 114, pp. 469-470.
Liu & Sylvester, "The Inhibitory Effect of 9-Amino-1,2,3,4-Tetrahydroacridine (THA) on Platelet Function", Thrombosis Research (1992), V. 67, pp. 533-544.
Kanaho, et al., "Mechanism of Inhibitory Effect of Some Amphiphilic Drugs on Platelet Aggregation Induced by Collagen, Thrombin or Arachidonic Acid", Thrombosis Research (1983), V. 31, pp. 817-831.
Beebe, et al., "A New Pharmacological Treatment for Intermittent Claudication: Results of a Randomized, Multicenter Trial", Archives of Internal Medicine (1999), V. 159, pp. 2041-2050.
DeVos, et al., "Cellular Pharmacology of Cerulenin Analogs that Inhibit Protein Palmitoylation", Biochemical Pharmacology (2001), V. 62, pp. 985-995.
Hirose, et al., "Antithrombotic Activity of NSP-513, a Novel Selective Phosphodiesterase 3 Inhibitor, on Femoral Arterial Thrombosis Induced by Physical Stenosis and Electrical Current: Comparison of Antithrombotic and Hemodynamic Effects", Journal of Cardiovascular Pharmacology (2000), V. 35, pp. 586-594.
Jacob, et al., "Endothelial Cell Apoptosis is Accelerated by Inorganic Iron and Heat Via an Oxygen Radical Dependent Mechanism", Surgery (1997), V. 122, pp. 243-254.
Papayianni, et al., "Transcellular Biosynthesis of Lipoxin $A_4$ During Adhesion of Platelets and Neutrophils in Experimental Immune Complex Glomerulonephritis", Kidney International (1995), V. 47, pp. 1295-1302.
Chen, et al., "Effects of CI-930, a Novel Phosphodiesterase III Inhibitor, on Platelt Aggregation and Arahidonic Acid Metabolism", Acta Pharmacologica Sinica (1990), V. 11, pp. 338-343.

(Continued)

*Primary Examiner*—Brian Kwon
(74) *Attorney, Agent, or Firm*—Kathleen M. Williams; Mark J. FitzGerald; Edwards Angell Palmer & Dodge, LLP

(57) ABSTRACT

The invention provides methods and compositions for reducing platelet activation, platelet aggregation and thrombosis. The invention further provides compositions and methods for treating or preventing diseases or disorders in which the pathology of the disease or disorder involves one or more of platelet activation, platelet aggregation and thrombus formation. The invention additionally relates to the use of protein palmitoylation inhibitors for the reduction of platelet activation, platelet aggregation and thrombosis, as well as to the use of protein palmitoylation as a target for the identification of inhibitors of platelet activation, platelet aggregation and thrombosis.

1 Claim, 17 Drawing Sheets

OTHER PUBLICATIONS

Yamakodo, et al., "Mepacrine-Induced Inhibition of Human Platelet Cyclic-GMP Phosphodiesterase", BBA-Biochimica Biophysica Acta (1984), V. 801, pp. 111-116.

Sloan, et al., "Protein Kinase C-Dependent and $Ca^{2+}$-Dependent Mechanisms of Secretion from Streptolysin O-Permeabilized Platelets: Effects of Leakage of Cytosolic Proteins", Biochemical Journal (1997), V. 328, pp. 13-21.

van Willigen & Akkerman, Protein Kinase C and Cyclic AMP Regulate Reversible Exposure of Binding Sites for Fibrinogen on the Glycoprotein IIB-IIIA Complex of Human Platelets, Biochemical Journal (1991), V. 273, pp. 115-120.

White & Raynor, "The Effect of Phenothiazine and Non-Phenothiazine Inhibitors of Calmodulin on Platelet Calcium Fluxes", Biochemical and Biophysical Research Communications (1982), V. 104, pp. 1066-1072.

Chung, et al., "Protein Kinase C Phosphorylation of Syntaxin 4 in Thrombin-Activated Human Platelets", Journal of Biological Chemistry (2000), V. 275, No. 33, pp. 25286-25291.

Fratti, et al., Endothelial Cell Injury Caused by *Candida Albicans* Is Dependent on Iron, Infection and Immunity (1998), V. 66, pp. 191-196.

Hirose, et al., "Antiplatelet and Antithrombotic Effects of a Novel Selective Phosphodiesterase 3 Inhibitor, NSP-513, in Mice and Rats", Japanese Journal of Pharmacology (2000), V. 82, pp. 188-198.

Rosen, et al., "Laser-Induced Noninvasive Vascular Injury Models in Mice Generate Platelet- and Coagulation-Dependent Thrombi", American Journal of Pathology (2001), V. 158, No. 5, pp. 1613-1622.

Brufani, et al., "Synthesis of Phenothiazine Derivatives as Potential Inhibitors of Phospholipase C.", Farmaco (1992), V. 47, pp. 585-597.

Rinder & Fitch, "Amplification of the Inflammatory Response: Adhesion Molecules Associated with Platelet/White Cell Responses", Journal of Cardiovascular Pharmacology (1996), V. 27, Suppl. 1, pp. 6-12.

\* cited by examiner

9-methylene-4-(alkyl)-2,3,4,9-tetrahydro-1H-cyclopenta(b)quinoline

Active

Not Active

Active                                                Not Active acetic acid 3-(2,4-dichlorophenyl)-3-oxo-
1-trichloromethyl-propyl ester

Active

Not Active

[1,10] Phenanthrolines

Active

[1,10] phenanthroline-ylamine

[1,10] phenanthroline

Not Active

[4,7] phenanthroline

[1,7] phenanthroline

10H-phenothiazine, 10-(4-morpholinylacetyl)-2-(trifluoromethyl)

Active

Not Active

2-(4-Oxo-cyclohexa-2,5-dienylideneamino)-isoindole-1,3-dione

Active

Not Active

5-furan-2-ylmethylene-1-naphthalen-1-yl-pyrimidine-2,4,6-trione

Active

Not Active

JF081204{3C}
IC$_{50}$ = 150 µM

JF081204{4C}
IC$_{50}$ = 10 µM

JF081204{5C}
IC$_{50}$ = 2 µM

METHODS FOR REDUCING PLATELET ACTIVATION PLATELET AGGREGATON OR THROMBOSIS

RELATED APPLICATIONS

This application is a continuation-in-part of PCT/US02/19843, which was filed Jun. 24, 2002, was published in English on Jan. 9, 2003, and designated the United States. PCT/US02/19843 claimed the priority of U.S. provisional application No. 60/300,932, filed Jun. 26, 2001. These priority documents are incorporated herein by reference in their entirety.

FIELD OF THE INVENTION

The invention relates to antithrombotic agents and their use for the treatment and prevention of diseases or disorders characterized by platelet activation.

BACKGROUND OF THE INVENTION

Platelet accumulation at sites of vascular injury is a dynamic process that mediates formation of both the primary hemostatic plug and pathologic thrombus formation. The mechanisms by which platelet surface proteins direct platelet recruitment to thrombi under flow conditions have been studied in detail (Ruggeri et al., 1999, *Blood* 94, 172–8; Savage et al., 1998, *Cell* 94, 657–66). In addition to directing initial platelet adhesion, cell-surface receptor interactions activate intracellular signaling (Yap et al., 2002, *Blood* 99, 151–8). Intracellular signaling stimulates the release of thrombogenic substances from platelet granules. Signaling also mediates activation of the platelet integrin $a_{11b}\beta_3$ that facilitates firm adhesion of platelets to thrombi (Nesbitt et al., 2002, *J Biol Chem* 277, 2965–72; Schoenwaelder et al., 2002, *J Biol Chem* 5, 5).

Arterial thrombosis mediates tissue infarction in coronary artery disease, cerebrovascular disease, and peripheral vascular disease, and, thus, is the single most common cause of morbidity and mortality in the United States. Platelets are key mediators of arterial thrombosis. Thus, the identification of compounds that inhibit platelet function is of great importance to medicine.

Platelets form the body's primary means of hemostasis and, as such, have developed an elaborate mechanism of surveying the vasculature for defects in endothelial integrity. This mechanism involves the ability to respond to subendothelial matrices (Savage et al., 1998, *Cell* 94, 657–666), shear forces (Fredrickson et al., 1998, *Blood* 92, 3684–3693), neighboring platelets (Shattil et al., 1985, *Blood* 66, 92–98), the adrenal axis (Larsson et al., 1992, *Thromb Haemost* 68, 687–693), as well as soluble proteinacious, nucleotide, and lipid signals. Despite this plethora of physiologic activators, the platelet has only a small repertoire of major functional outputs. Upon activation, platelets change shape, aggregate, and secrete their granular contents. The process of platelet activation involves the expression of activities not shared by functionally merit resting platelets, including, for example, ATP release, serotonin release, lysosomal release, alpha granule release, dense granule release, and cell surface expression of markers of activated platelets (including, but not limited to CD9, GPIb, GPIIb, GPIIIa, CDIa-IIa, P-selectin, PECAM-1, activated GPIIb/IIIa, and vitronectin receptor). In addition, platelet activation results in the aggregation of platelets with each other and with non-platelet surrounding cells. The granular contents of platelets supply additional adhesion molecules, growth factors, coagulation enzymes and other specialized molecules instrumental in the process of thrombus formation and the initiation of the healing process.

In addition to coronary artery disease/myocardial infarction, cerebrovascular disease and peripheral vascular disease, diseases and disorders associated with inappropriate platelet activity and arterial thrombosis also include, for example, stable and unstable angina, transient ischemic attacks, placental insufficiency, unwanted thromboses subsequent to surgical procedures (e.g., aortocoronary bypass surgery, angioplasty and stent placement, and heart valve replacement), or thromboses subsequent to atrial fibrillation. Inhibitors of platelet activity can provide therapeutic and preventive benefits for each of these diseases or disorders. It is also possible that inappropriate platelet activation plays a role in venous thrombosis, such that platelet inhibitors can be useful for the treatment or prevention of disorders associated with such thromboses.

A connection is emerging between platelet activation and inflammation, particularly allergic inflammation (e.g., in asthma) and inflammation at the sites of atherosclerotic damage. See, for example: Rinder & Fitch, 1996, *J Cardiovasc Pharmacol* 27, Suppl. 1:S6–12 (investigating the role of complement components in activation of platelet and polymorphonuclear neutrophils by cardiopulmonary bypass); Palabrica et al., 1992, *Nature* 359, 848–851 (P-selectin mediates leukocyte adhesion to platelets in vivo, and the bound leukocytes promote fibrin deposition); Papayianni et al., 1995, *Kidney Int* 47, 1295–1302 (reduction of platelets reduces generation of immune modulator lipoxin A4 generation during experimental immune complex-mediated glomerulonephritis); Bazzoni et al., 1991, *Haematologica* 76, 491–499 (review describing the elaborate cross-talk between platelets and neutrophils in thrombotic and inflammatory diseases); and Kazura, 1989, *J Lab Clin Med* 114, 469–470 (editorial on the platelet-neutrophil interaction and modulation of the inflammatory response). Therefore, compounds that inhibit platelet activation can also be useful in the treatment or prevention of disorders involving inflammation.

There are a number of agents presently available that target platelet function. For example, aspirin is a relatively weak platelet inhibitor. However, aspirin can cause life-threatening allergic reactions in sensitive individuals.

Another platelet inhibiting agent is ticlopidine (Ticlid™, Roche Pharmaceuticals). Because it requires the production of active metabolites to be effective, the effect of ticlopidine is delayed 24–48 hours. The drug can also cause thrombotic thrombocytopenic purpura, a life-threatening condition, as well as nausea, abdominal pain, dyspepsia, diarrhea and skin rash.

Clodiprogel (Plavix™, Bristol-Meyers Squibb/Sanofi Pharmaceuticals) is another platelet inhibitor that requires the generation of active metabolites for its therapeutic efficacy. Therefore, clodiprogel also has a delay of 24–48 hours for its effect. Clodiprogel can also cause thrombotic thrombocytopenia purpura as well as agranulocytopenia, both life-threatening conditions. The drug has also been associated with rash, edema, hypertension, hypercholesterolemia, nausea, abdominal pain, dyspepsia, diarrhea, urinary tract infections, liver enzyme elevations and arthralgia.

The platelet inhibitory agents Abiximab and c7E3 Fab (Reopro abciximab™, manufacturer—Centocor B. V., distributor—Eli Lilly and Co.) are only available in a parenteral form. The drugs can cause severe thrombocytopenia. Both have a very long half-life and, therefore, complicate surgery that is sometimes required in the setting of life-threatening arterial occlusion (e.g., emergent cardiac surgery in the setting of a myocardial infarction).

Tirofiban (Aggrastat™, Merck and Co., Inc.) is another platelet inhibitory agent that is only available in a parenteral form. Tirofiban can cause thrombocytopenia, coronary artery dissection, bradycardia and edema, as well as dizziness and vasovagal reactions.

Eptifibatide (Integrilin™, COR Therapeutics, Inc., Key Pharmaceuticals Inc.) is another platelet inhibitory agent that is only available for parenteral administration. It can cause hypotension.

There is only limited clinical experience with the oral anti-GPIIbIIIa agents lamifiban, sibrafiban, orofiban and xemilofiban. Similarly, clinical experience is limited with the phosphodiesterase inhibitors cilostazol, trapidil and trifusal. There is more clinical experience with the phosphodiesterase inhibitor dipyridamole, but its activity is so weak that it is not frequently used.

There is a need in the art for additional platelet inhibitory agents for the treatment and prevention of diseases or disorders characterized by platelet activation and thrombosis.

SUMMARY OF THE INVENTION

The invention provides methods for reducing platelet activation, reducing platelet aggregation and reducing thrombosis. The invention further provides methods of treating or preventing diseases or disorders in which the pathology of the disease or disorder involves one or more of platelet activation, platelet aggregation and thrombus formation.

The invention encompasses a method of reducing platelet activation, platelet aggregation or thrombosis, the method comprising administering an effective amount of a compound having Structure 1 or a pharmaceutically acceptable salt thereof, such that platelet activation, aggregation or thrombosis is reduced,

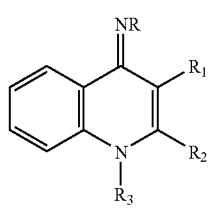

Structure 1 wherein:

R and $R_3$ are selected from the group consisting of H, linear or branched alkyl, aryl, aralkyl, alkenyl, heteroalkyl, heteroaryl, cycloalkyl, cycloalkenyl and substituted derivatives thereof; and $R_1$ and $R_2$ are selected from the group consisting of H, linear or branched alkyl, aralkyl, alkenyl, cycloalkyl, cycloalkenyl, alkoxy and substituted derivatives thereof, or wherein carbon atoms at $R_1$ and $R_2$ are bridged to form a substituted or unsubstituted cycloalkyl or cycloalkenyl ring.

In one embodiment, the compound having Structure 1 is selected from the group consisting of:

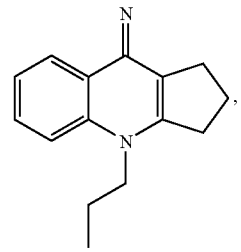

I

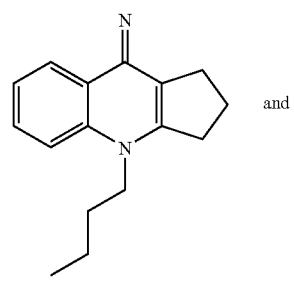

II and

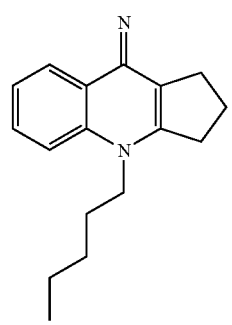

III or a pharmaceutically acceptable salt thereof.

The invention further encompasses a method of preventing or treating a disease or disorder characterized by platelet activation, platelet aggregation, or thrombosis, the method comprising administering to an individual suffering from such a disease or disorder an effective amount of a compound of Structure 1 or a pharmaceutically acceptable salt thereof, such that the disease or disorder is prevented or treated, wherein:

R and $R_3$ are selected from the group consisting of H, linear or branched alkyl, aryl, aralkyl, alkenyl, heteroalkyl, heteroaryl, cycloalkyl, cycloalkenyl and substituted derivatives thereof; and $R_1$ and $R_2$ are selected from the group consisting of H, linear or branched alkyl, aralkyl, alkenyl, cycloalkyl, cycloalkenyl, alkoxy and substituted derivatives thereof, or wherein carbon atoms at $R_1$ and $R_2$ are bridged to form a substituted or unsubstituted cycloalkyl or cycloalkenyl ring.

In one embodiment, the compound having Structure 1 is selected from the group consisting of:

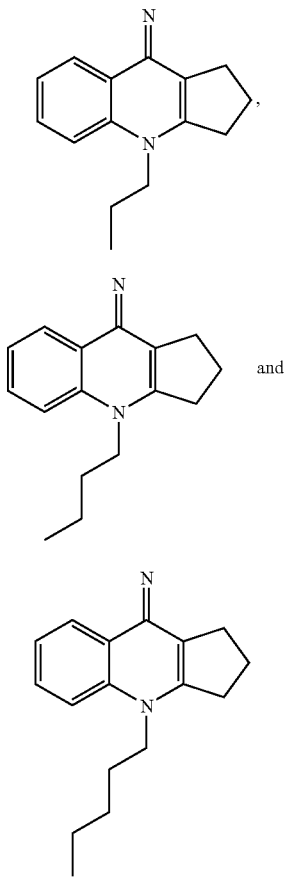

or a pharmaceutically acceptable salt thereof.

The invention further encompasses a method of treating or preventing a disease or disorder characterized by platelet activation, platelet aggregation or thrombosis, the method comprising the step of administering to an individual in need of such treatment or prevention:

(i) an effective amount of a compound of Structure 1 or a pharmaceutically acceptable salt thereof, wherein:

R and $R_3$ are selected from the group consisting of H, linear or branched alkyl, aryl, aralkyl, alkenyl, heteroalkyl, heteroaryl, cycloalkyl, cycloalkenyl and substituted derivatives thereof; and $R_1$ and $R_2$ are selected from the group consisting of H, linear or branched alkyl, aralkyl, alkenyl, cycloalkyl, cycloalkenyl, alkoxy and substituted derivatives thereof, or wherein carbon atoms at $R_1$ and $R_2$ are bridged to form a substituted or unsubstituted cycloalkyl or cycloalkenyl ring; and (ii) a compound selected from the group consisting of aspirin, ticlopidine, clopidrogel, Abiximab, c7E3 Fab, Tirofiban, Eptifibatide, an anti-GPIIbIIIa agent, and a phosphodiesterase inhibitor, such that the disease or disorder is treated or prevented.

In one embodiment of these aspects of the invention, the substituted derivatives comprise one or more chemical substituents selected from the group consisting of halogen, $NO_2$, $NH_2$, $CO_2R^4$, $COR^4$ and $OR^4$, wherein $R^4$ is H or alkyl. In a preferred embodiment, $R_3$ is lower alkyl.

In another embodiment, the disease or disorder is selected from the group consisting of acute myocardial infarction; stable angina; unstable angina; transient ischemic attack; cerebrovascular disease; peripheral vascular disease; placental insufficiency; thrombosis subsequent to or associated with a surgical procedure; thrombosis associated with atrial fibrillation; and inflammation. In a preferred embodiment, the inflammation is inflammation associated with wound healing, atherosclerosis or allergy. In another preferred embodiment, the surgical procedure is selected from the group consisting of aortocoronary bypass surgery; coronary angioplasty; stent placement; and insertion of prosthetic heart valves.

The invention further encompasses a pharmaceutical composition comprising a first agent selected from the group consisting of aspirin, ticlopidine, clopidrogel, Abiximab, c7E3 Fab, Tirofiban, Eptifibatide, an anti-GPIIbIIIa agent, and a phosphodiesterase inhibitor, and a second agent of Structure 1 or a pharmaceutically acceptable salt thereof, wherein:

R and $R_3$ are selected from the group consisting of H, linear or branched alkyl, aryl, aralkyl, alkenyl, heteroalkyl, heteroaryl, cycloalkyl, cycloalkenyl and substituted derivatives thereof, and $R_1$ and $R_2$ are selected from the group consisting of H, linear or branched alkyl, aralkyl, alkenyl, cycloalkyl, cycloalkenyl, alkoxy and substituted derivatives thereof, or wherein carbon atoms at $R_1$ and $R_2$ are bridged to form a substituted or unsubstituted cycloalkyl or cycloalkenyl ring. In one embodiment, the substituted derivatives comprise one or more chemical substituents selected from the group consisting of halogen, $NO_2$, $NH_2$, $CO_2R^4$, $COR^4$ and $OR^4$, wherein $R^4$ is H or alkyl. In another embodiment, $R_3$ is lower alkyl.

The invention further encompasses a method of reducing platelet activation, platelet aggregation or thrombosis, the method comprising administering an effective amount of a compound having Structure 2 or a pharmaceutically acceptable salt thereof:

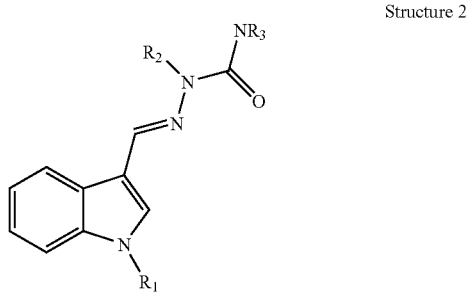

Structure 2 such that platelet activation, platelet aggregation or thrombosis is reduced, wherein $R_1$, $R_2$ and $R_3$ are selected from:

H, linear or branched alkyl, aryl, aralkyl, alkenyl, heteroalkyl, heteroaryl, cycloalkyl, cycloalkenyl and substituted derivatives thereof.

The invention further encompasses a method of treating or preventing a disease or disorder characterized by platelet activation, platelet aggregation or thrombosis, the method comprising administering to an individual suffering from such a disease or disorder an effective amount of a compound of Structure 2 or a pharmaceutically acceptable salt thereof, such that the disease or disorder is treated or prevented, wherein $R_1$, $R_2$ and $R_3$ are selected from:

H, linear or branched alkyl, aryl, aralkyl, alkenyl, heteroalkyl, heteroaryl, cycloalkyl, cycloalkenyl and substituted derivatives thereof.

The invention further encompasses a method of treating or preventing a disease or disorder characterized by platelet activation, platelet aggregation or thrombosis, the method comprising the step of administering to an individual in need of such treatment or prevention:

(i) an effective amount of compound of Structure 2 or a pharmaceutically acceptable salt thereof, such that the disease or disorder is treated or prevented, wherein $R_1$, $R_2$ and $R_3$ are selected from:

H, linear or branched alkyl, aryl, aralkyl, alkenyl, heteroalkyl, heteroaryl, cycloalkyl, cycloalkenyl and substituted derivatives thereof; and (ii) a compound selected from the group consisting of: aspirin, ticlopidine, clopidrogel, Abiximab, c7E3 Fab, Tirofiban, Eptifibatide, an anti-GPIIbIIIa agent, and a phosphodiesterase inhibitor, such that the disease or disorder is treated or prevented.

In one embodiment of the above aspects of the invention, the substituted derivatives comprise one or more chemical substituents selected from the group consisting of halogen, $NO_2$, $NH_2$, $CO_2R^4$, $COR^4$ and $OR^4$, wherein $R_1$ is H or alkyl.

In another embodiment of these aspects, the compound having Structure 2 comprises Structure 3 or a pharmaceutically acceptable salt thereof.

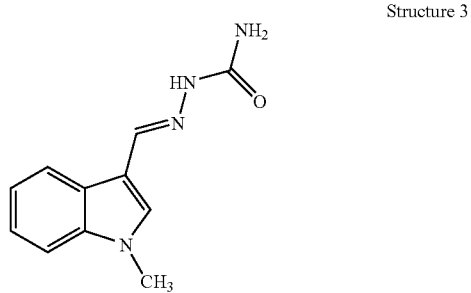

Structure 3

In another embodiment, the disease or disorder is selected from the group consisting of: acute myocardial infarction; stable angina; unstable angina; transient ischemic attack; cerebrovascular disease; peripheral vascular disease; placental insufficiency; atrial fibrillation; thrombosis associated with a surgical procedure; and inflammation. In a preferred embodiment, the inflammation is inflammation associated with wound healing, atherosclerosis, or allergy. In another preferred embodiment, the surgical procedure is selected from the group consisting of: aortocoronary bypass surgery; coronary angioplasty; stent placement; and insertion of prosthetic heart valves.

The invention further encompasses a pharmaceutical composition comprising a first agent selected from the group consisting of: aspirin, ticlopidine, clopidrogel, Abiximab, c7E3 Fab, Tirofiban, Eptifibatide, an anti-GPIIbIIIa agent, and a phosphodiesterase inhibitor; and a second agent of Structure 2 or a pharmaceutically acceptable salt thereof, wherein $R_1$, $R_2$ and $R_3$ are selected from:

H, linear or branched alkyl, aryl, aralkyl, alkenyl, heteroalkyl, heteroaryl, cycloalkyl, cycloalkenyl and substituted derivatives thereof.

In one embodiment, the substituted derivatives comprise one or more chemical substituents selected from the group consisting of halogen, $NO_2$, $NH_2$, $CO_2R^4$, $COR^4$ and $OR^4$, wherein $R^4$ is H or alkyl.

The invention further encompasses a method of reducing platelet activation, platelet aggregation, or thrombosis, the method comprising administering an effective amount of a compound having Structure 4 or a pharmaceutically acceptable salt thereof:

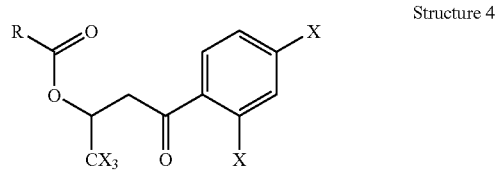

Structure 4 such that platelet activation, platelet aggregation or thrombosis is reduced, wherein X is H or halogen and wherein R is H, linear or branched alkyl, aryl, aralkyl, alkenyl, heteroalkyl, heteroaryl, cycloalkyl, cycloalkenyl and substituted derivatives thereof.

The invention further encompasses a method of treating or preventing a disease or disorder characterized by platelet activation, platelet aggregation or thrombosis, the method comprising administering to an individual in need of such treatment or prevention an effective amount of a compound of Structure 4 or a pharmaceutically acceptable salt thereof, wherein X is H or halogen and wherein R is H, linear or branched alkyl, aryl, aralkyl, alkenyl, heteroalkyl, heteroaryl, cycloalkyl, cycloalkenyl and substituted derivatives thereof, such that the disease or disorder is prevented or treated.

The invention further encompasses a method of treating or preventing a disease or disorder characterized by platelet activation, the method comprising the step of administering to an individual in need of such treatment or prevention:

(i) an effective amount of a compound of Structure 4 or a pharmaceutically acceptable salt thereof, wherein X is H or halogen and wherein R is H, linear or branched alkyl, aryl, aralkyl, alkenyl, heteroalkyl, heteroaryl, cycloalkyl, cycloalkenyl and substituted derivatives thereof; and (ii) a compound selected from the group consisting of: aspirin, ticlopidine, clopidrogel, Abiximab, c7E3 Fab, Tirofiban, Eptifibatide, an anti-GPIIbIIIa agent, and a phosphodiesterase inhibitor, such that the disease or disorder is treated or prevented.

In one embodiment of the above aspects of the invention, the substituted derivatives comprise one or more chemical substituents selected from the group consisting of halogen, $NO_2$, $NH_2$, $CO_2R^4$, $COR^4$ and $OR^4$, wherein $R^4$ is H or alkyl.

In another embodiment, the compound having Structure 4 is a compound having Structure 5 or a pharmaceutically acceptable salt thereof:

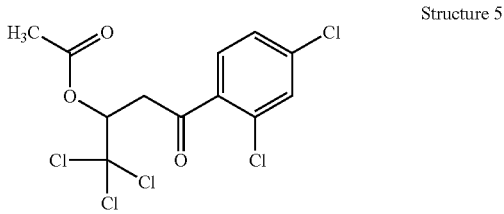

Structure 5

In another embodiment, the disease or disorder is selected from the group consisting of: acute myocardial infarction; stable angina; unstable angina; transient ischemic attack; cerebrovascular disease; peripheral vascular disease; placental insufficiency; atrial fibrillation; thrombosis associated with a surgical procedure; and inflammation. In a preferred embodiment, the disease or disorder is inflammation associated with wound healing, atherosclerosis, or allergy. In another preferred embodiment, the surgical procedure is selected from the group consisting of: aortocoronary bypass surgery; coronary angioplasty; stent placement; and insertion of prosthetic heart valves.

The invention further encompasses a pharmaceutical composition comprising a first agent selected from the group consisting of: aspirin, ticlopidine, clopidrogel, Abiximab, c7E3 Fab, Tirofiban, Eptifibatide, an anti-GPIIbIIIa agent, and a phosphodiesterase inhibitor, and a second agent of Structure 4 or a pharmaceutically acceptable salt thereof, wherein X is H or halogen and wherein R is H, linear or branched alkyl, aryl, aralkyl, alkenyl, heteroalkyl, heteroaryl, cycloalkyl, cycloalkenyl and substituted derivatives thereof.

In one embodiment, the substituted derivatives comprise one or more chemical substituents selected from the group consisting of halogen, $NO_2$, $NH_2$, $CO_2R^4$, $COR^4$ and $OR^4$, wherein $R^4$ is H or alkyl.

The invention further encompasses a method of reducing platelet activation, platelet aggregation or thrombosis, the method comprising administering an effective amount of a compound having Structure 6 or a pharmaceutically acceptable salt thereof

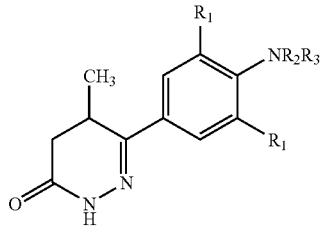

Structure 6 wherein $R_1$ is H or $NO_2$ and at least one of $R_1$ is $NO_2$, and wherein $R_2$ and $R_3$ are the same or different and are selected from the group consisting of H, linear or branched alkyl, aryl, aralkyl, alkenyl, heteroalkyl, heteroaryl, cycloalkyl, cycloalkenyl and substituted derivatives thereof, or a compound having Structure 7 or a pharmaceutically acceptable salt thereof

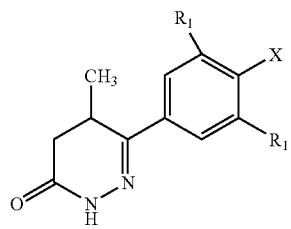

Structure 7 wherein $R_1$ is H or $NO_2$ and wherein X is halogen, such that platelet activation, platelet aggregation or thrombosis is reduced.

The invention further encompasses a method of treating or preventing a disease or disorder characterized by platelet activation, platelet aggregation or thrombosis, the method comprising administering an effective amount of a compound of Structure 6 or a pharmaceutically acceptable salt thereof, wherein $R_1$ is H or $NO_2$ and at least one of $R_1$ is $NO_2$, and wherein $R_2$ and $R_3$ are the same or different and are selected from the group consisting of H, linear or branched alkyl, aryl, aralkyl, alkenyl, heteroalkyl, heteroaryl, cycloalkyl, cycloalkenyl and substituted derivatives thereof, or a compound of Structure 7 or a pharmaceutically acceptable salt thereof, wherein $R_1$ is H or $NO_2$ and wherein X is halogen, such that platelet activation is reduced, whereby the disease or disorder is treated or prevented.

The invention further encompasses a method of treating or preventing a disease or disorder characterized by platelet activation, platelet aggregation or thrombosis, the method comprising the step of administering to an individual in need of such treatment or prevention a first compound of Structure 6 or a pharmaceutically acceptable salt thereof, wherein $R_1$ is H or $NO_2$ and at least one of $R_1$ is $NO_2$, and wherein $R_2$ and $R_3$ are the same or different and are selected from the group consisting of H, linear or branched alkyl, aryl, aralkyl, alkenyl, heteroalkyl, heteroaryl, cycloalkyl, cycloalkenyl and substituted derivatives thereof, or a first compound of Structure 7 or a pharmaceutically acceptable salt thereof, wherein $R_1$ is H or $NO_2$ and wherein X is halogen, and a second compound selected from the group consisting of: aspirin, ticlopidine, clopidrogel, Abiximab, c7E3 Fab, Tirofiban, Eptifibatide, an anti-GPIIbIIIa agent, and a phosphodiesterase inhibitor, such that the disease or disorder is treated or prevented.

In one embodiment of these aspects of the invention, the substituted derivatives comprise one or more chemical substituents selected from the group consisting of halogen, $NO_2$, $NH_2$, $CO_2R^4$, $COR^4$ and $OR^4$, wherein $R^4$ is H or alkyl.

In another embodiment, the compound having Structure 6 or 7 has Structure 8 or 9, respectively, or a pharmaceutically acceptable salt thereof:

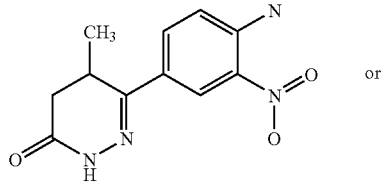

Structure 8 or

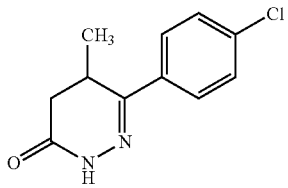

Structure 9

In another embodiment, the disease or disorder is selected from the group consisting of: acute myocardial infarction; stable angina; unstable angina; transient ischemic attack; cerebrovascular disease; peripheral vascular disease; placental insufficiency; thrombosis subsequent to or associated with a surgical procedure; thrombosis associated with atrial fibrillation; and inflammation. In a preferred embodiment, the inflammation is inflammation associated with wound healing, atherosclerosis or allergy. In another preferred embodiment, the surgical procedure is selected from the group consisting of: aortocoronary bypass surgery; coronary angioplasty; stent placement; and insertion of prosthetic heart valves.

The invention further encompasses a pharmaceutical composition comprising a first agent selected from the group consisting of: aspirin, ticlopidine, clopidrogel, Abiximab, c7E3 Fab, Tirofiban, Eptifibatide, an anti-GPIIbIIIa agent, and a phosphodiesterase inhibitor, and a second agent of Structure 6 or a pharmaceutically acceptable salt thereof, wherein $R_1$ is H or $NO_2$ and at least one of $R_1$ is $NO_2$, and wherein $R_2$ and $R_3$ are the same or different and are selected from the group consisting of H, linear or branched alkyl, aryl, aralkyl, alkenyl, heteroalkyl, heteroaryl, cycloalkyl, cycloalkenyl and substituted derivatives thereof, or a second agent of Structure 7 or a pharmaceutically acceptable salt thereof, wherein $R_1$ is H or $NO_2$ and wherein X is halogen.

In one embodiment, the substituted derivatives comprise one or more chemical substituents selected from the group consisting of halogen, $NO_2$, $NH_2$, $CO_2R^4$, $COR^4$ and $OR^4$, wherein $R^4$ is H or alkyl.

The invention further encompasses a method of reducing platelet activation, platelet aggregation or thrombosis, the method comprising administering an effective amount of a compound having Structure 10 or a pharmaceutically acceptable salt thereof

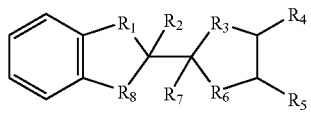

Structure 10 such that platelet activation, platelet aggregation or thrombosis is reduced, wherein:

$R_1$, $R_3$, $R_6$ and $R_8$ are selected from the group consisting of $CH_2$, C=O, and $C(OR)_2$, wherein R=H, linear or branched alkyl, aryl, aralkyl, alkenyl, heteroalkyl, heteroaryl, cycloalkyl, cycloalkenyl or substituted derivatives thereof; and $R_4$ and $R_5$ are selected from the group consisting of H, linear or branched alkyl, linear or branched alkenyl, or combine with the carbon atoms to which they are bonded to form a cycloalkyl or cycloalkenyl ring or aromatic ring and substituted derivatives thereof.

The invention further encompasses a method of treating or preventing a disease or disorder characterized by platelet activation, platelet aggregation or thrombosis, the method comprising administering to an individual suffering from such a disease or disorder an effective amount of a compound of Structure 10 or a pharmaceutically acceptable salt thereof, wherein:

$R_1$, $R_3$, $R_6$ and $R_8$ are selected from the group consisting of $CH_2$, C=O, and $C(OR)_2$, wherein R=H, linear or branched alkyl, aryl, aralkyl, alkenyl, heteroalkyl, heteroaryl, cycloalkyl, cycloalkenyl or substituted derivatives thereof; and $R_4$ and $R_5$ are selected from the group consisting of H, linear or branched alkyl, linear or branched alkenyl, or combine with the carbon atoms to which they are bonded to form a cycloalkyl, cycloalkenyl or aromatic ring and substituted derivatives thereof, whereby the disease or disorder is treated or prevented.

The invention further encompasses a method of treating or preventing a disease or disorder characterized by platelet activation, platelet aggregation or thrombosis, the method comprising the step of administering to an individual in need of such treatment or prevention:

(i) a first compound of Structure 10 or a pharmaceutically acceptable salt thereof, wherein:

$R_1$, $R_3$, $R_6$ and $R_8$ are selected from the group consisting of $CH_2$, C=O, and $C(OR)_2$, wherein R=H, linear or branched alkyl, aryl, aralkyl, alkenyl, heteroalkyl, heteroaryl, cycloalkyl, cycloalkenyl and substituted derivatives thereof; and $R_4$ and $R_5$ are selected from the group consisting of H, linear or branched alkyl, linear or branched alkenyl, or combine with the carbon atoms to which they are bonded to form a cycloalkyl, cycloalkenyl or aromatic ring, and substituted derivatives thereof; and (ii) a second compound selected from the group consisting of: aspirin, ticlopidine, clopidrogel, Abiximab, c7E3 Fab, Tirofiban, Eptifibatide, an anti-GPIIbIIIa agent, and a phosphodiesterase inhibitor, such that the disease or disorder is treated or prevented.

In one embodiment of the above aspects of the invention, the substituted derivatives comprise one or more chemical substituents selected from the group consisting of halogen, $NO_2$, $NH_2$, $CO_2R^4$, $COR^4$ and $OR^4$, wherein $R^4$ is H or alkyl.

In another embodiment, the compound having Structure 10 comprises a compound of Structure 11 or a pharmaceutically acceptable salt thereof:

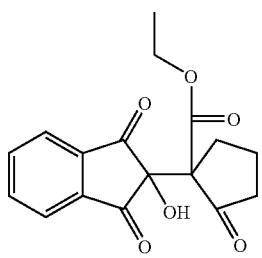

Structure 11

In another embodiment, the disease or disorder is selected from the group consisting of: acute myocardial infarction; stable angina; unstable angina; transient ischemic attack; cerebrovascular disease; peripheral vascular disease; placental insufficiency; thrombosis subsequent to or associated with a surgical procedure; thrombosis associated with atrial fibrillation; and inflammation. In a preferred embodiment, the inflammation is inflammation associated with wound healing, atherosclerosis or allergy. In another preferred embodiment, the surgical procedure is selected from the group consisting of: aortocoronary bypass surgery; coronary angioplasty; stent placement; and insertion of prosthetic heart valves.

The invention further encompasses a pharmaceutical composition comprising a first agent selected from the group consisting of: aspirin, ticlopidine, clopidrogel, Abiximab, c7E3 Fab, Tirofiban, Eptifibatide, an anti-GPIIbIIIa agent, and a phosphodiesterase inhibitor, and a second agent of Structure 10 or a pharmaceutically acceptable salt thereof, wherein:

$R_1$, $R_3$, $R_6$ and $R_8$ are selected from the group consisting of $CH_2$, C=O, and $C(OR)_2$, wherein R=H, linear or branched alkyl, aryl, aralkyl, alkenyl, heteroalkyl, heteroaryl, cycloalkyl, cycloalkenyl or substituted derivatives thereof; and $R_4$ and $R_5$ are selected from the group consisting of H, linear or branched alkyl, linear or branched alkenyl, or combine with the carbon atoms to which they are bonded to form a cycloalkyl or cycloalkenyl ring, aromatic ring and substituted derivatives thereof.

In one embodiment, the substituted derivatives comprise one or more chemical substituents selected from the group consisting of halogen, $NO_2$, $NH_2$, $CO_2R^4$, $COR^4$ and $OR^4$, wherein $R^4$ is H or alkyl.

The invention further encompasses a method of reducing platelet activation, platelet aggregation or thrombosis, the method comprising administering an effective amount of a compound having Structure 12 or a pharmaceutically acceptable salt thereof

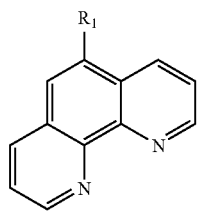

Structure 12 such that platelet activation, platelet aggregation or thrombosis is reduced, wherein R is selected from H, linear or branched alkyl, aryl, aralkyl, alkenyl, heteroalkyl, heteroaryl, cycloalkyl, cycloalkenyl or substituted derivatives thereof, or primary, secondary or tertiary amine, such that platelet activation, aggregation or thrombosis is reduced.

The invention further encompasses a method of treating or preventing a disease or disorder characterized by platelet activation, platelet aggregation or thrombosis, the method comprising administering to an individual in need of such treatment or prevention an effective amount of a compound of Structure 12 or a pharmaceutically acceptable salt thereof, wherein R is selected from H, linear or branched alkyl, aryl, aralkyl, alkenyl, heteroalkyl, heteroaryl, cycloalkyl, cycloalkenyl or substituted derivatives thereof, or primary, secondary or tertiary amine, whereby the disease or disorder is treated or prevented.

The invention further encompasses a method of treating or preventing a disease or disorder characterized by platelet activation, platelet aggregation or thrombosis, the method comprising the step of administering to an individual in need of such treatment or prevention a first compound of Structure 12 or a pharmaceutically acceptable salt thereof, wherein R is selected from H, linear or branched alkyl, aryl, aralkyl, alkenyl, heteroalkyl, heteroaryl, cycloalkyl, cycloalkenyl or substituted derivatives thereof, or primary, secondary or tertiary amine, and a second compound selected from the group consisting of: aspirin, ticlopidine, clopidrogel, Abiximab, c7E3 Fab, Tirofiban, Eptifibatide, an anti-GPIIbIIIa agent, and a phosphodiesterase inhibitor, such that the disease or disorder is treated or prevented.

In one embodiment of the above aspects of the invention, the substituted derivatives comprise one or more chemical substituents selected from the group consisting of halogen, $NO_2$, $NH_2$, $CO_2R^4$, $COR^4$ and $OR^4$, wherein $R^4$ is H or alkyl.

In another embodiment, the compound having Structure 12 comprises Structure 13 or a pharmaceutically acceptable salt thereof:

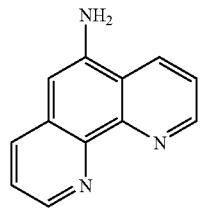

Structure 13

In another embodiment, the disease or disorder is selected from the group consisting of: acute myocardial infarction; stable angina; unstable angina; transient ischemic attack; cerebrovascular disease; peripheral vascular disease; placental insufficiency; thrombosis subsequent to or associated with a surgical procedure; thrombosis associated with atrial fibrillation; and inflammation. In a preferred embodiment, the inflammation is inflammation associated with wound healing, atherosclerosis or allergy. In another preferred embodiment, the surgical procedure is selected from the group consisting of: aortocoronary bypass surgery; coronary angioplasty; stent placement; and insertion of prosthetic heart valves.

The invention further encompasses a pharmaceutical composition comprising a first agent selected from the group consisting of: aspirin, ticlopidine, clopidrogel, Abiximab, c7E3 Fab, Tirofiban, Eptifibatide, an anti-GPIIbIIIa agent, and a phosphodiesterase inhibitor, and a second agent of Structure 12 or a pharmaceutically acceptable salt thereof, wherein R is selected from H, linear or branched alkyl, aryl, aralkyl, alkenyl, heteroalkyl, heteroaryl, cycloalkyl, cycloalkenyl or substituted derivatives thereof, or primary, secondary or tertiary amine.

In one embodiment, the substituted derivatives comprise one or more chemical substituents selected from the group consisting of halogen, $NO_2$, $NH_2$, $CO_2R^4$, $COR^4$ and $OR^4$, wherein $R^4$ is H or alkyl.

The invention further encompasses a method of reducing platelet activation, platelet aggregation or thrombosis, the method comprising administering an effective amount of a compound having Structure 14 or a pharmaceutically acceptable salt thereof:

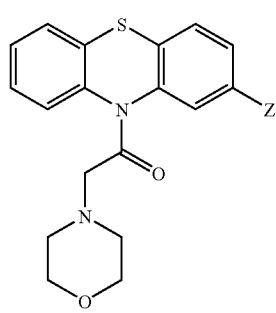

Structure 14 such that platelet activation, platelet aggregation or thrombosis is reduced, wherein Z can be H or $CR_1R_2R_3$, and wherein $R_1$, $R_2$, and $R_3$ can be H, halogen, linear or branched alkyl, aryl, aralkyl, alkenyl, heteroalkyl, heteroaryl, cycloalkyl, cycloalkenyl or substituted derivatives thereof.

The invention further encompasses a method of treating or preventing a disease or disorder characterized by platelet activation, platelet aggregation or thrombosis, the method comprising administering an effective amount of a compound having Structure 14 or a pharmaceutically acceptable salt thereof, wherein Z can be H or $CR_1R_2R_3$, and wherein $R_1$, $R_2$, and $R_3$ can be H, halogen, linear or branched alkyl, aryl, aralkyl, alkenyl, heteroalkyl, heteroaryl, cycloalkyl, cycloalkenyl or substituted derivatives thereof, such that the disease or disorder is treated or prevented.

The invention further encompasses a method of treating or preventing a disease or disorder characterized by platelet activation, platelet aggregation or thrombosis, the method comprising the step of administering to an individual in need of such treatment or prevention:

(i) a first compound of Structure 14 or a pharmaceutically acceptable salt thereof, wherein Z can be H or $CR_1R_2R_3$, and wherein $R_1$, $R_2$, and $R_3$ can be H, halogen, linear or branched alkyl, aryl, aralkyl, alkenyl, heteroalkyl, heteroaryl, cycloalkyl, cycloalkenyl or substituted derivatives thereof; and (ii) a second compound selected from the group consisting of: aspirin, ticlopidine, clopidrogel, Abiximab, c7E3 Fab, Tirofiban, Eptifibatide, an anti-GPIIbIIIa agent, and a phosphodiesterase inhibitor, such that the disease or disorder is treated or prevented.

In one embodiment of these aspects of the invention, the substituted derivatives comprise one or more chemical substituents selected from the group consisting of halogen, $NO_2$, $NH_2$, $CO_2R^4$, $COR^4$ and $OR^4$, wherein $R^4$ is H or alkyl.

In another embodiment, the compound having Structure 14 comprises Structure 15 or a pharmaceutically acceptable salt thereof:

Structure 15

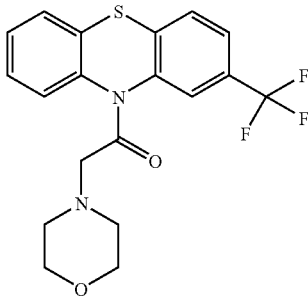

In another embodiment, the disease or disorder is selected from the group consisting of: acute myocardial infarction; stable angina; unstable angina; transient ischemic attack; cerebrovascular disease; peripheral vascular disease; placental insufficiency; thrombosis subsequent to or associated with a surgical procedure; thrombosis associated with atrial fibrillation; and inflammation. In a preferred embodiment, the inflammation is inflammation associated with wound healing, atherosclerosis or allergy. In another preferred embodiment, the surgical procedure is selected from the group consisting of: aortocoronary bypass surgery; coronary angioplasty; stent placement; and insertion of prosthetic heart valves.

The invention further encompasses a pharmaceutical composition comprising a first agent selected from the group consisting of: aspirin, ticlopidine, clopidrogel, Abiximab, c7E3 Fab, Tirofiban, Eptifibatide, an anti-GPIIbIIIa agent, and a phosphodiesterase inhibitor; and a second agent of Structure 14 or a pharmaceutically acceptable salt thereof, wherein Z can be H or $CR_1R_2R_3$, and wherein $R_1$, $R_2$, and $R_3$ can be H, halogen, linear or branched alkyl, aryl, aralkyl, alkenyl, heteroalkyl, heteroaryl, cycloalkyl, cycloalkenyl or substituted derivatives thereof.

In one embodiment, the substituted derivatives comprise one or more chemical substituents selected from the group consisting of halogen, $NO_2$, $NH_2$, $CO_2R^4$, $COR^4$ and $OR^4$, wherein $R^4$ is H or alkyl.

The invention further encompasses a method of reducing platelet activation, platelet aggregation or thrombosis, the method comprising administering an effective amount of a compound having Structure 16, or a pharmaceutically acceptable salt thereof:

Structure 16

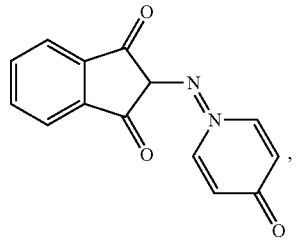

such that platelet activation, platelet aggregation or thrombosis is reduced.

The invention further encompasses a method of treating or preventing a disease or disorder characterized by platelet activation, platelet aggregation or thrombosis, the method comprising administering to an individual in need of such treatment or prevention an effective amount of a compound of Structure 16, or a pharmaceutically acceptable salt thereof, such that platelet activation, platelet aggregation or thrombosis is reduced, whereby the disease or disorder is treated.

The invention further encompasses a method of treating or preventing a disease or disorder characterized by platelet activation, platelet aggregation or thrombosis, the method comprising the step of administering to an individual in need of such treatment or prevention a first compound of Structure 16, or a pharmaceutically acceptable salt thereof, and a second compound selected from the group consisting of: aspirin, ticlopidine, clopidrogel, Abiximab, c7E3 Fab, Tirofiban, Eptifibatide, an anti-GPIIbIIIa agent, and a phosphodiesterase inhibitor, such that the disease or disorder is treated or prevented.

In another embodiment, the disease or disorder is selected from the group consisting of: acute myocardial infarction; stable angina; unstable angina; transient ischemic attack; cerebrovascular disease; peripheral vascular disease; placental insufficiency; thrombosis subsequent to or associated with a surgical procedure; thrombosis associated with atrial fibrillation; and inflammation. In a preferred embodiment, the inflammation is inflammation associated with wound healing, atherosclerosis or allergy. In another preferred embodiment, the surgical procedure is selected from the group consisting of: aortocoronary bypass surgery; coronary angioplasty; stent placement; and insertion of prosthetic heart valves.

The invention further encompasses a pharmaceutical composition comprising a first agent selected from the group consisting of: aspirin, ticlopidine, clopidrogel, Abiximab, c7E3 Fab, Tirofiban, Eptifibatide, an anti-GPIIbIIIa agent, and a phosphodiesterase inhibitor, and a second agent of Structure 16, or a pharmaceutically acceptable salt thereof.

The invention further encompasses a method of reducing platelet activation, platelet aggregation or thrombosis, the method comprising administering an effective amount of a compound having Structure 17 or a pharmaceutically acceptable salt thereof:

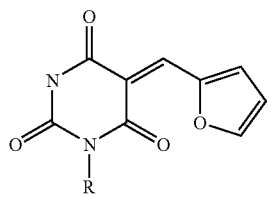

Structure 17 wherein R is an aromatic or heteroaromatic group, or a substituent or derivative thereof, such that platelet activation, platelet aggregation or thrombosis is reduced.

The invention further encompasses a method of treating or preventing a disease or disorder characterized by platelet activation, platelet aggregation or thrombosis, the method comprising administering to an individual suffering from such a disease or disorder an effective amount of a compound of Structure 17, or a pharmaceutically acceptable salt thereof wherein R is an aromatic or heteroaromatic group, or a substituent or derivative thereof, such that platelet activation, platelet aggregation or thrombosis is reduced, whereby the disease or disorder is treated or prevented.

The invention further encompasses a method of treating or preventing a disease or disorder characterized by platelet activation, the method comprising the step of administering to an individual in need of such treatment or prevention a first compound of Structure 17, pharmaceutically acceptable salt thereof wherein R is R is an aromatic or heteroaromatic group, or a substituent or derivative thereof, and a second compound selected from the group consisting of: aspirin, ticlopidine, clopidrogel, Abiximab, c7E3 Fab, Tirofiban, Eptifibatide, an anti-GPIIbIIIa agent, and a phosphodiesterase inhibitor, such that the disease or disorder is treated or prevented.

In one embodiment of these aspects of the invention, the substituent or derivative comprises one or more chemical substituents selected from the group consisting of halogen, $NO_2$, $NH_2$, $CO_2R^4$, $COR^4$ and $OR^4$, wherein $R^4$ is H or alkyl.

In another embodiment, R is phenyl, anthracene or phenanthrene.

In another embodiment, the compound having Structure 17 comprises Structure 18 or a pharmaceutically acceptable salt thereof:

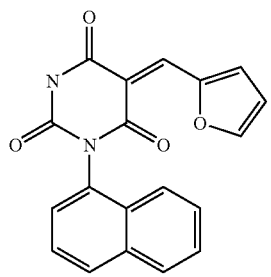

Structure 18

In another embodiment, the disease or disorder is selected from the group consisting of: acute myocardial infarction; stable angina; unstable angina; transient ischemic attack; cerebrovascular disease; peripheral vascular disease; placental insufficiency; thrombosis subsequent to or associated with a surgical procedure; thrombosis associated with atrial fibrillation; and inflammation. In a preferred embodiment, the inflammation is inflammation associated with wound healing, atherosclerosis or allergy. In another preferred embodiment, the surgical procedure is selected from the group consisting of: aortocoronary bypass surgery; coronary angioplasty; stent placement; and insertion of prosthetic heart valves.

The invention further encompasses a pharmaceutical composition comprising a first agent selected from the group consisting of: aspirin, ticlopidine, clopidrogel, Abiximab, c7E3 Fab, Tirofiban, Eptifibatide, an anti-GPIIbIIIa agent, and a phosphodiesterase inhibitor, and a second agent of Structure 17, or a pharmaceutically acceptable salt thereof wherein R is an aromatic or heteroaromatic group or substutuent or derivative thereof.

In one embodiment, the substituent or derivative comprises one or more chemical substituents selected from the group consisting of halogen, $NO_2$, $NH_2$, $CO_2R^4$, $COR^4$ and $OR^4$, wherein $R^4$ is H or alkyl.

In another embodiment, R is phenyl, anthracene or phenanthrene.

In another aspect, the invention encompasses a method of reducing platelet activation, platelet aggregation or thrombosis, the method comprising administering an effective amount of a palmitoylation inhibitor, such that platelet activation, platelet aggregation or thrombosis is reduced.

In one embodiment, the palmitoylation inhibitor comprises a compound of Structure 1 or a pharmaceutically acceptable salt thereof:

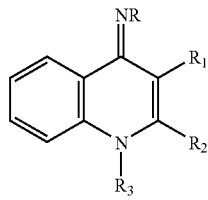

Structure 1 wherein:

R and $R_3$ are selected from the group consisting of H, linear or branched alkyl, aryl, aralkyl, alkenyl, heteroalkyl, heteroaryl, cycloalkyl, cycloalkenyl and substituted derivatives thereof, and $R_1$ and $R_2$ are selected from the group consisting of H, linear or branched alkyl, aralkyl, alkenyl, cycloalkyl, cycloalkenyl, alkoxy and substituted derivatives thereof, or wherein carbon atoms at $R_1$ and $R_2$ are bridged to form a substituted or unsubstituted cycloalkyl or cycloalkenyl ring.

In another embodiment, $R_3$ comprises a linear alkyl chain comprising 3, 4 or 5 carbons.

In another embodiment, the palmitoylation inhibitor comprises a compound having one of the following structures:

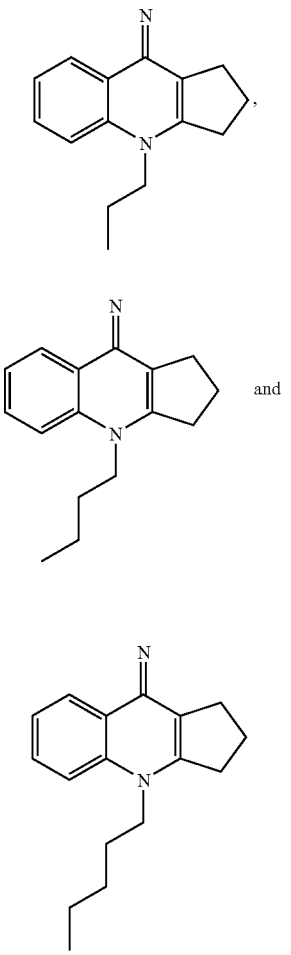

In another embodiment, the palmitoylation inhibitor comprises a compound having the following structure:

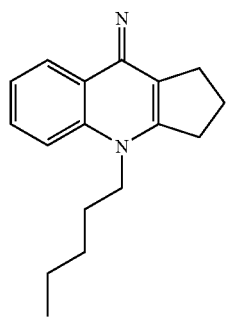

In another aspect, the invention encompasses a method of treating or preventing a disease or disorder characterized by platelet activation, platelet aggregation or thrombosis, the method comprising administering to an individual an effective amount of a palmitoylation inhibitor, such that platelet activation, platelet aggregation or thrombosis is reduced.

In one embodiment, the palmitoylation inhibitor comprises a compound of Structure 1 or a pharmaceutically acceptable salt thereof:

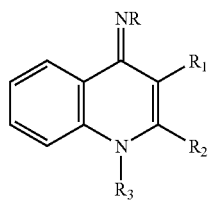

Structure 1 wherein:

R and $R_3$ are selected from the group consisting of H, linear or branched alkyl, aryl, aralkyl, alkenyl, heteroalkyl, heteroaryl, cycloalkyl, cycloalkenyl and substituted derivatives thereof, and $R_1$ and $R_2$ are selected from the group consisting of H, linear or branched alkyl, aralkyl, alkenyl, cycloalkyl, cycloalkenyl, alkoxy and substituted derivatives thereof, or wherein carbon atoms at $R_1$ and $R_2$ are bridged to form a substituted or unsubstituted cycloalkyl or cycloalkenyl ring.

In another embodiment, $R_3$ comprises a linear alkyl chain comprising 3, 4 or 5 carbons.

In another embodiment of this or the previous aspect, the substituted derivatives comprise one or more chemical substituents selected from the group consisting of halogen, $NO_2$, $NH_2$, $CO_2R^4$, $COR^4$ and $OR^4$, wherein $R^4$ is H or alkyl.

In another embodiment, the palmitoylation inhibitor comprises a compound having one of the following structures:

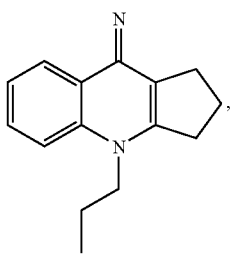

I

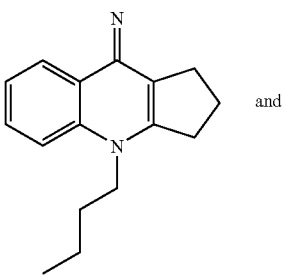

and

II

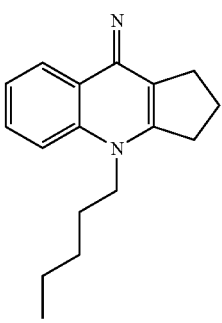

III

In another embodiment, the palmitoylation inhibitor comprises a compound having the following structure:

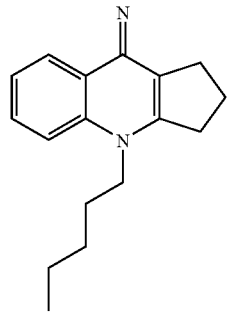

In another aspect, the invention encompasses a method of identifying an inhibitor of platelet activation, platelet aggregation or thrombosis, the method comprising: a) providing a source of palmitoyl acetyltransferase and a palmitoylation substrate; b) contacting the palmitoylation substrate with palmitoyl CoA, and palmitoyl acetyltransferase in the presence and absence of a candidate inhibitor of platelet activation, platelet aggregation or thrombosis; and c) measuring palmitoylation of the substrate, wherein a decrease in the amount of palmitoylation in the presence of the candidate inhibitor, relative to the absence of the candidate inhibitor identifies the candidate as an inhibitor of platelet activation, platelet aggregation or thrombosis.

As used herein, the term "platelet activation" refers to the process whereby a functionally resting platelet is stimulated to secrete one or more factors involved in thrombus formation or inflammation, or to aggregate. The process of platelet activation involves the expression of activities not shared by functionally resting platelets, including, for example, ATP release, serotonin release, cell surface expression of markers of activated platelets (including, but not limited to P-selectin and activated GPIIb/IIIa). Alternatively, "platelet activation" is defined herein as the ability of platelets to aggregate with each other. The term "platelet activation" is used herein to refer to the process whereby a platelet gains the expression any one or more of these activities.

As used herein, "activated" platelets express at least 25% of the level of ATP release exhibited by platelets treated with a 100 µM final concentration of the platelet agonist SFLLR in a luciferin/luciferase assay as described herein. Alternatively, "activated" platelets express at least 25% of the level of serotonin release exhibited by platelets treated with 100 µM SFLLR SFLLR in a $^{14}$C serotonin release assay as described herein. As a further alternative measure, "activated" platelets express at least 25% of the level of cell surface P-selectin and/or activated GPIIbIIIa as platelets treated with 100 µM SFLLR in a flow cytometry assay. As a final alternative, "activated platelets" exhibit at least 25% of the aggregation detected after 6 minutes in an aggregation assay of PRP (from an individual not treated with platelet inhibitor), treated with 200 µM SFLLR peptide, as described herein. An activated platelet can, and most likely will, express other markers of platelet activation, including, but not limited to CD9, GPIb, GPIIb, GPIIIa, CDIa-IIa, P-selectin, PECAM-1, GPIIb/IIIa, vitronectin receptor, and other integrins and adhesive molecules.

As used herein, a compound is a "platelet inhibitor" if it results in at least a 50% inhibition of platelet activity at a concentration of 100 µM or lower in a given assay, relative to platelet activity in the absence of the compound.

As used herein, platelet activity or platelet activation is "reduced" if the level of activity is at least 25% lower in the presence of an inhibitor than in the absence of that inhibitor. Because numerous diseases or disorders involve platelet activation, platelet aggregation and/or thrombosis, a reduction in any or all of these processes can be used to treat or prevent such diseases or disorders. Diseases or disorders involving platelet activities, platelet aggregation or thrombosis include, but are not limited to acute myocardial infarction; stable angina; unstable angina; transient ischemic attack; cerebrovascular disease; peripheral vascular disease; placental insufficiency; atrial fibrillation; thrombosis associated with a surgical procedure; and inflammation.

As used herein, the term "platelet aggregation" refers to the adhesion of activated platelets to one another that results in the formation of aggregates or clumps of activated platelets. Platelet aggregation is measured using an aggregometer, which measures the increase in the transmittance of light as platelet aggregation occurs. Platelets are "aggregated" if there is an increase in light transmittance of at least 25% by 6 minutes after the addition of the platelet agonist SFLLR 200 µM in an aggregation assay as described herein relative to light transmittance prior to agonist addition.

As used herein, the term "thrombosis" refers to the formation or development of a thrombus. Thrombosis in a patient can be monitored by angiography, MRI or CAT scanning. "Reduced thrombosis" means either that there is no growth or increase in size of one or more thrombi, or that one or more thrombi has become smaller (e.g., by at least 10%, preferably by at least 20%, 35%, 50%, 75%, 85%, 90%, 95% or even up to and including 100%, or no detectable thrombus).

As used herein, the term "antithrombotic activity" refers to a compound that reduces thrombosis as defined herein above.

Therefore as used herein, the term "disease or disorder characterized by platelet activation" refers to a disease or disorder in which platelet activation is a characteristic, but not limited to thrombosis and inflammation. It is noted that platelet activation is key in the process of thrombus formation, but that platelet activation is also involved in diseases or disorders where the symptoms are not necessarily caused by thrombosis, e.g., inflammation. Thus, the term "platelet activation" is a characteristic of both thrombosis and inflammation.

Platelet aggregation is key in the process of thrombosis formation, but platelet aggregation is also involved in diseases or disorders where the symptoms are not necessarily caused by thrombosis, e.g., inflammation. Thus, platelet aggregation is a characteristic of both thrombosis and inflammation. Therefore, as used herein, the term "disease or disorder characterized by platelet aggregation" refers to a disease or disorder in platelet aggregation is a characteristic of both thrombosis and inflammation.

As used herein, the term "disease or disorder characterized by thrombosis" refers to a disease or disorder in which one or more aspects of the pathology is caused by the presence or formation of one or more thrombi.

As used herein, the term "thrombosis associated with a surgical procedure" refers to the formation of one or more thrombi either during or following a surgical procedure, where such thrombi are clinically undesirable. By "clinically undesirable" is meant that the thrombi pose a threat to the health or recovery of the individual.

As used herein, the term "anti-GPIIbIIIa agent" refers to a compound that inhibits the activation of platelet GPIIbIIIa as detected by activation-specific anti-GPIIbIIIa antibodies. GPIIbIIIa activity is "inhibited" if agonist-induced activation in the presence of a known or suspected inhibitor is reduced by 25% or more relative to a sample lacking the known or suspected inhibitor.

As used herein, the term "phosphodiesterase inhibitor" refers to a compound that inhibits platelet phosphodiesterase activity as detected by augmentation of $PGE_1$-stimulated cAMP production in platelets. A compound is a phosphodiesterase inhibitor if it results in a 2-fold or greater increase in $PGE_1$-stimulated cAMP level.

As used herein, the phrase "palmitoylation inhibitor" refers to a compound that inhibits the incorporation of $^3H$-palmitate into acid-precipitable protein by at least 10% relative to the same assay performed without the compound. A palmitoylation inhibitor preferably inhibits the incorporation of palmitate into protein by at least 20%, or more, e.g., 30%, 40%, 50%, 60%, 70%, 80%, 90% or more, up to and including 100%. Non-limiting examples of palmitoylation inhibitors include, for example, the compound having the structures:

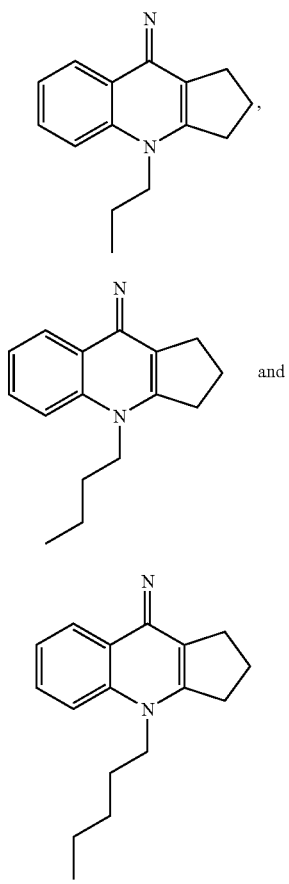

as well as 2-bromopalmitic acid, cerulenin ([2R,3S]-2,3-epoxy-4-oxo-7,10-trans, trans-dodecadienamide; DeVos et al., 2001, Biochem. Pharmacol. 62: 985–995), cis-2,3-epoxy-4-oxododecanamide (DeVos et al., supra), cis-2,3-epoxy-4-oxononadecanamide (DeVos et al., supra) and tunicamycin.

As used herein, the term "cell permeant" means that a platelet inhibiting compound useful according to the invention is able to cross the cell membrane of living cells. The calculated logP is an estimation of cell permeability. LogP is the log of the partition coefficient in octanol/water, and a value of zero denotes equal partitioning between the two phases. A "cell permeant" compound as used herein has a logP value between 0 and 5, inclusive. It is noted that while the platelet inhibitory compounds useful according to the invention are cell permeant, the compounds do not necessarily have to penetrate the cell in order to function. For example, a compound that interferes with ligand binding to the thrombin receptor can act without penetrating the cell.

As used herein, the term "lipophilic" means that a platelet inhibiting compound preferentially (i.e., >50%) partitions to the lipid compartment of a mixture of lipid and non-lipid components.

As used herein, the term "alkyl" means a linear or branched chain, saturated, aliphatic hydrocarbon radical containing one to 20 carbon atoms. The term "cycloalkyl" refers to saturated, carbocyclic, hydrocarbon radicals having three to eight carbon atoms.

As used herein, the term "lower alkyl" means a linear or branched alkyl chain of 1 to 5 carbon atoms. Non-limiting examples of lower alkyl groups include methyl, ethyl, n-propyl, isopropyl, n-butyl, isobutyl, sec-butyl and tert-butyl.

A pharmaceutical composition comprises a pharmacologically effective amount of an active agent and a pharmaceutically acceptable carrier. As used herein, "pharmacologically effective amount," "therapeutically effective amount" or simply "effective amount" refers to that amount of an agent effective to produce the intended pharmacological, therapeutic or preventive result. For example, if a given clinical treatment is considered effective when there is at least a 25% reduction in a measurable parameter associated with a disease or disorder, a therapeutically effective amount of a drug for the treatment of that disease of disorder is the amount necessary to effect that at least 25% reduction. The term "pharmaceutically acceptable carrier" refers to a carrier for administration of a therapeutic agent, such as platelet inhibitor compounds useful according to the invention. Such carriers include, but are not limited to, saline, buffered saline, dextrose, water, glycerol, ethanol, and combinations thereof. The term specifically excludes cell culture medium. For drugs administered orally, pharmaceutically acceptable carriers include, but are not limited to pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

As used herein, the term "sustained decrease" refers to a decrease in a measurable parameter that lasts at least 24 hours.

As used herein, the term "pharmaceutically acceptable salt" refers to salts of the subject compounds which possess the desired pharmacological activity and which are neither biologically nor otherwise undesirable. The salts can be formed with inorganic acids such as acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemisulfate heptanoate, hexanoate, hydrochloride hydrobromide, hydroiodide, 2-hydroxyethanesulfonate, lactate, maleate, methanesulfonate, 2-naphthalenesulfonate, nicotinate, oxalate, thiocyanate, tosylate and undecanoate. Base salts include ammonium salts, alkali metal salts such as sodium and potassium salts, alkaline earth metal salts such as calcium and magnesium salts, salt with organic bases such as dicyclohexylamine salts, N-methyl-D-glucamine, and salts with amino acids such as arginine, lysine, and so forth. Also, the basic nitrogen-containing groups can be quarternized with such agents as lower alkyl halides, such as methyl, ethyl, propyl, and butyl chloride, bromides and iodides; dialkyl sulfates like dimethyl, diethyl, dibutyl and diamyl sulfates, long chain halides such as decyl, lauryl, myristyl and stearyl chlorides, bromides and iodides, aralkyl halides like benzyl and phenethyl bromides and others. Water or oil-soluble or dispersible products are thereby obtained.

As used herein, the term "candidate inhibitor" refers to a compound to be tested for an inhibitory effect on an activity of interest, such as palmitoylation or platelet activation. Candidate inhibitors, particularly small molecule candidate inhibitors, can be drawn from any of a wide variety of commercially available compound libraries, or they can be generated using, for example, various combinatorial chemistry approaches well known to those of skill in the art.

Alternatively, known inhibitory compounds or compounds known to interact with a desired target can be modified as desired to generate new candidate molecules with improved characteristics (e.g., improved specific activity, solubility, binding, etc.).

BRIEF DESCRIPTION OF THE FIGURES

Each of the figures shows the results of structure/function studies performed using compounds structurally related to those initially identified as active against platelets.

(A) Thromboembolic events distal from the thrombus were captured using quantitative intravital fluorescence videomicroscopy with high temporal resolution( (111 frames/second) and the total amount of thromboembolization was calculated by determining the total fluorescence intensity of the fluorescently labeled platelets in thromboemboli. (B) Thromboembolization was recorded before infusion of pyridazinone compound. Platelet accumulation into thrombus is indicated by the gray line. Thromboembolism from the same thrombus is measured over time and is indicated by black bars. Each black bar represents a single thromboembolic event of the indicated fluorescent intensity. (C) Thromboembolization after infusion of 1.2 mg/kg pyridizinone was significantly reduced.

Figure 12:
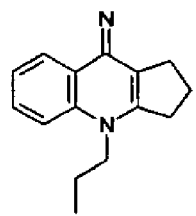
Figure 12:
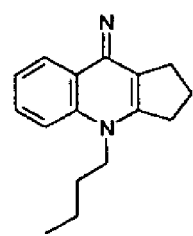
Figure 12:
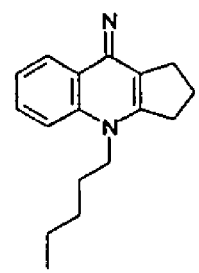

FIG. 12 shows the structures of the JF081204 compounds and their respective $IC_{50}$'s in SFLLRN-induced P-selectin expression assays using flow cytometry.

Figure 13:
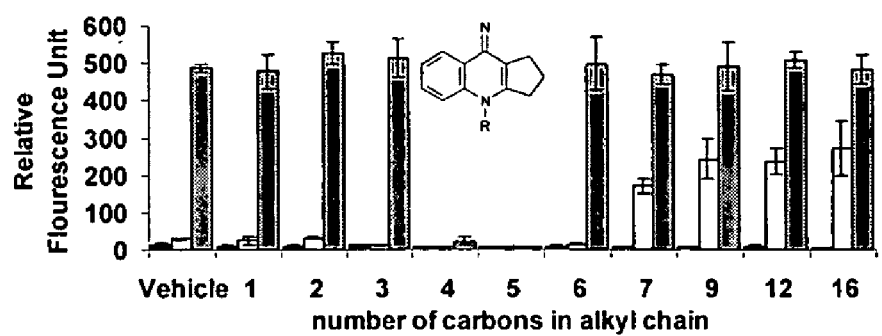

FIG. 13 shows the results of experiments in which the length of the alkyl tail of the JF081204 compounds was varied. Platelets were incubated with 30 µM of the indicated JF081204 compound. Platelets were then stimulated with 0 µM, 20 µM, or 200 µM of SFLLRN and assayed for P-selectin surface expression as determined by flow cytometry. JF081204 compounds with a 4- or 5-carbon chain, but not with shorter or longer carbon chain, inhibited platelet activation stimulated by a maximal dose of 200 µM SFLLRN. JF081204 compounds with a 7-carbon or longer chain augmented P-selectin expression in the presence of a submaximal dose of 20 µM SFLLRN. This augmentation was SFLLRN activation-dependent.

FIG. 14a–b shows the effect of JF081204 {5C} on protein palmitoylation in platelets. Platelets were labeled with [$^3$H]-palmitate for 2 hours in the absence (lanes 1, 2, and 3) or presence (lanes 4, 5, and 6) of 100 µM JF081204{5C} for 2 hours. Labeled platelets were then incubated with 0 µM (lanes 1 and 3), 20 µM (lanes 2 and 5), or 200 µM SFLLRN (lanes 3 and 6). Platelet samples were lysed, separated by SDS-PAGE, Western blotted, and visualized with a tritium imager screen (Panel a). The activation of platelets by SFLLRN led to an increase incorporation of [$^3$H]-palmitate into platelet proteins, whereas the presence of JF081204{5C} inhibited this activation-dependent [$^3$H]-palmitate incorporation (Panel b). Western blot membrane from panel (a) was stained with Ponceau S to visualize proteins in the platelet lysates.

Figure 15:
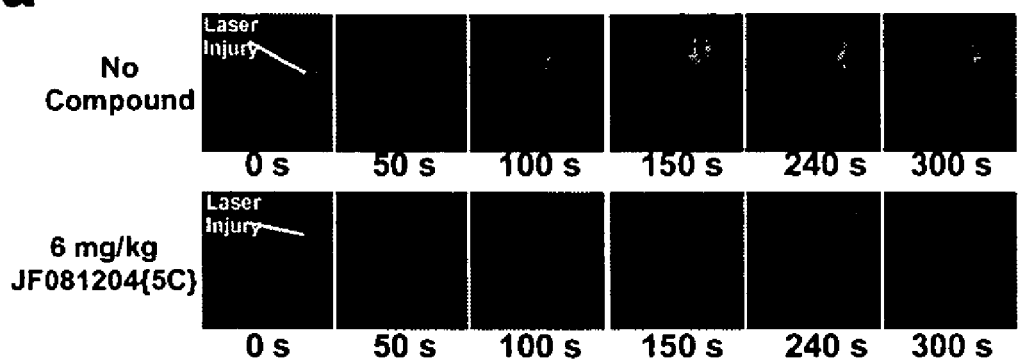
Figure 15:
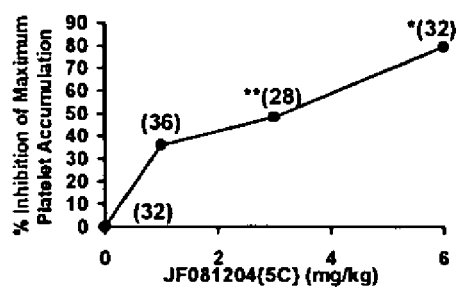
Figure 15:
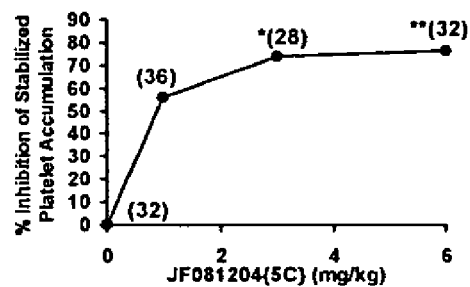

FIG. 15a–b shows the effect of JF081204{5C} inhibition of palmitoylation on platelet accumulation into thrombi. Post-infusion thrombi and the matching pre-infusion thrombi constituting a pair were compared for statistical analysis using the Wilcoxon rank sum test. (a) A representative experiment showing fluorescence microscopy images of platelet accumulation into thrombus at various times after laser injury without (top panel) and with (lower panel) infusion of JF081204{5C}. The infusion of JF081204{5C} led to a significant inhibition of platelet accumulation into thrombus. (b) In the presence of 3 mg/kg ($P<0.002$) and 6 mg/kg ($P<0.02$) of JF081204{5C}, a statistically significant decrease in the median of maximum platelet accumulation compared to the absence of JF081204{5C} was observed. (c) A dose-dependent inhibition of the median stabilized platelet accumulation was also observed in the presence of 3 mg/kg ($P<0.01$) and 6 mg/kg ($P<0.001$) of JF081204{5C}.

Figure 16:
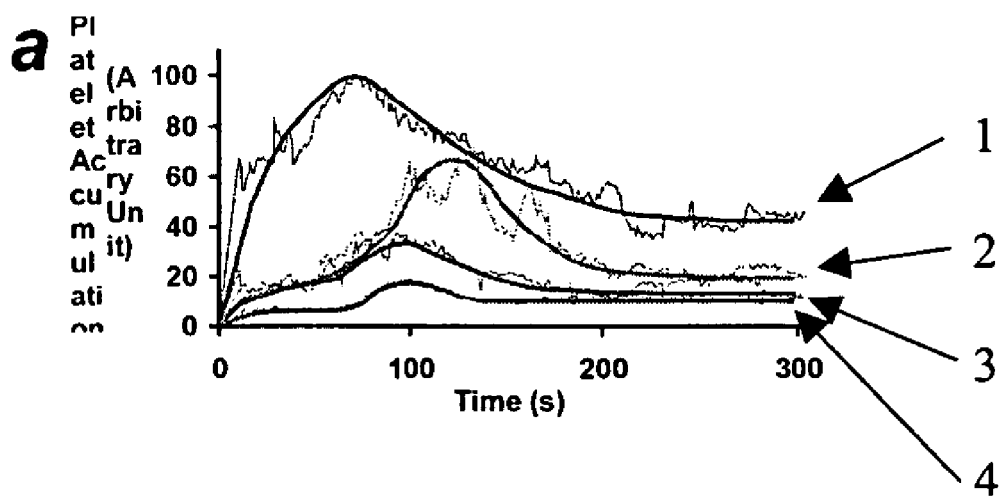
Figure 16:
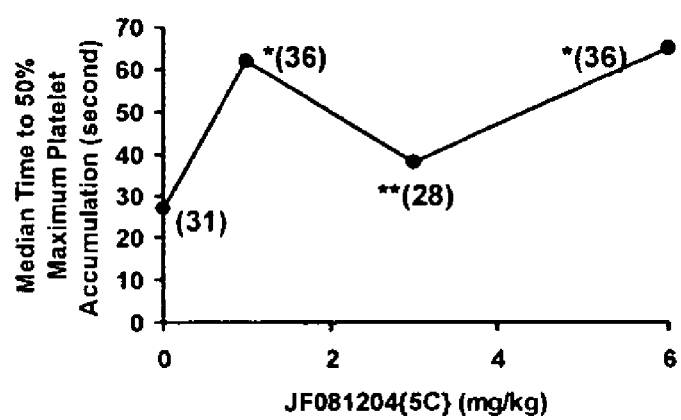

FIG. 16a–b shows a kinetic analysis of platelet accumulation in thrombi following laser-induced endothelial cell injury in the presence of JF081204{5C}. (a) Thrombi were generated before and after infusion of either vehicle control (line 1, n=32), 1 mg/kg (line 2, n=36), 3 mg/kg (line 3, n=28) or 6 mg/kg JF081204{5C} (line 4, n=36). Median fluorescence values of the indicated number of thrombi were calculated at each dose of JF081204{5C}. One arbitrary unit was defined as 1% of the maximum fluorescent intensity of the maximum thrombus size induced by control injury. (b) In the presence of 1 mg/kg ($P<0.001$), 3 mg/kg ($P<0.05$) and 6 mg/kg ($P<0.001$) of JF081204{5C}, a statistically significant delay in the onset of platelet accumulation compared to the absence of JF081204{5C} was observed.

DETAILED DESCRIPTION OF THE INVENTION

The invention relates to the identification of several new classes of platelet inhibitors useful for reducing inappropriate platelet activation. The identified platelet inhibitors have the advantage that they are lipophilic, meaning that they may be effective in oral preparations and that they may have a large volume of distribution. Assays for the measurement of platelet activation and thrombus formation are described below, as are the details of how to make and use the compounds identified herein as platelet inhibitors.

The invention further relates to the use of inhibitors of palmitoylation as inhibitors of platelet activation and thrombosis and the use of palmitoylation as a target to screen for antithrombotics.

Assays for Platelet Inhibitory Activity

Because there are a number of physical and chemical changes that occur when platelets are activated, there are a number of assays available for the measurement of platelet activation. For example, stimulated platelets release ATP and serotonin, which can be measured using various assays. Activated platelets also express distinct cell surface markers which can be readily monitored by flow cytometry. In addition, platelet aggregation is also routinely monitored. Also, for the development or evaluation of new drugs it is important to have an in vivo model of thrombosis. Details necessary to perform these various assays are described below.

In order to monitor the effect of known or suspected inhibitors of platelet activation, assays are performed in the presence of a known agonist of platelet activation. Examples of platelet agonists useful for such studies include, for example, the thrombin mimic peptide SFLLR (serine-phenylalanine-leucine-leucine-arginine), the thromboxane A2 mimic U46619, ADP, and the phorbol ester PMA.

Platelet Activation Assays

1. Assay for ATP Release.

For each of the assays described herein that use platelet rich plasma (PRP), the reagent can be prepared by mixing trisodium citrate (3.8%) and whole blood in a 1:9 ratio immediately after drawing the blood. The mixture is then centrifuged at 200g for 20 minutes, leaving PRP in the supernatant. Another source is PRP isolated by leukopheresis. If necessary, platelet count is determined using a Coulter Counter ZM (Coulter Co., Hialeah, Fla.).

In order to monitor ATP release, a cocktail of 100 µM SFLLR (synthesized using solid phase Fmoc chemistry on an Applied Biosystems model 430A peptide synthesizer) and 3 mg/ml of luciferin/luciferase (Sigma, St. Louis, Mo.) in a volume of 10 µl is added to 20 µl of PRP. Samples are immediately analyzed for luminescence. Activated platelets supply the ATP necessary for luminescence of the luciferin/luciferase assay. Assays can be performed at high throughput through use of a microtiter plate system, e.g., 384-well plates and a Multidrop 384 (Thermo Labsystems, Helsinki), read with a high density imaging system, e.g., the Tundra system (Imaging Research, St. Catherine's, Ontario).

In order to evaluate the inhibition of platelet activation by a known or suspected platelet inhibitor, one can pre-incubate the platelets (PRP) with varying concentrations (generally 1–100 µM) of the inhibitor for 30 min at room temperature prior to the addition of the SFLLR and luciferin/luciferase mixture.

Platelets are considered "activated" if they secrete at least 25% of the level of ATP secreted by PRP treated with a final concentration of 100 µM SFLLR peptide, where ATP secretion is measured by the luciferin/luciferase assay. Platelet activation is considered "reduced" if the level of ATP released by a sample of platelets, as measured by the SFLLR-induced luciferin/luciferase assay, is reduced by 25% or more in the presence of an inhibitor and SFLLR, relative to the presence of SFLLR alone.

2. Serotonin Release Assay.

Release of serotonin by platelets upon activation can be monitored by pre-labeling platelets (in PRP) at room temperature with 125 cpm of $^{14}$C-serotonin per μl of PRP for 30 min. After labeling, the platelets, e.g., 40 μl, are incubated with 100 μM SFLLR and 50 μM imipramine for 10 min. Platelets are then pelleted by centrifugation (3,000 g, 2 min), and $^{14}$C-serotonin in the supernatant is measured by scintillation counting, followed by calculation of the percentage of $^{14}$C-serotonin released (see, e.g., Hervig et al., 1990, *Clin Chem* 36, 28–31).

The effects of known or suspected inhibitors of platelet activation are measured by incubating various concentrations of the inhibitor with the labeled PRP for 30 min at room 10 temperature before the addition of SFLLR and imipramine.

By this assay, platelets are considered "activated" if they secrete at least 25% of the level of serotonin secreted by PRP treated with 100 μM SFLLR peptide. Platelet activation is considered "reduced" if the level of serotonin released by a sample of platelets in response to 100 μM SFLLR, as measured by a $^{14}$C serotonin release assay, is reduced by 25% or more in the presence of an inhibitor and SFLLR, relative to the presence of SFLLR alone.

3. Flow Cytometry Assays.

Activated platelets express a number of markers that permit their distinction from non-activated platelets, including, for example, CD9, GPIb, GPIIb, GPIIIa, CDIa-IIa, P-selectin, PECAM-1, GPIIb/IIIa, vitronectin receptor, and other integrins and adhesive molecules. Expression of any one or a combination of these molecules can be assayed by flow cytometry using antibodies specific for the chosen molecule(s). For example, activated platelets express P-selectin and activated GPIIbIIIa on their cell surfaces, both of which can be detected by specific antibodies.

In order to assay platelet activation by cell surface marker expression, fresh PRP is isolated from donors who have not ingested aspirin for two weeks prior to donation. PRP (40 μl) is incubated with known or suspected inhibitor in DMSO or DMSO alone for 15 min. The sample is then incubated with the indicated agonist (e.g., SFLLR) for 10 min. Following incubation of the sample with the indicated agonist, 10 μl of reaction mixture is transferred to 5 μl of phycoerythrin (PE)-conjugated AC 1.2 anti-P-selectin antibody (for assessment of P-selectin surface expression) or fluorescein isothiocyanate (FITC)-conjugated PAC-1 antibody (for assessment of GPIIbIIIa activation). PBS (500 μl) is added to the sample after a 20 min incubation and the platelets are analyzed immediately by flow cytometry. Flow cytometry can be performed using, for example, a Becton-Dickinson FACS-Calibur flow cytometer or its equivalent. Fluorescent channels are set at logarithmic gain. Ten thousand particles are acquired for each sample. A 530/30 band pass filter is used for FL-1 fluorescence. A 585/42 band pass filter is used for FL-2 fluorescence. FITC is measured in the FL-1 channel and PE is measured in the FL-2 channel. Data are analyzed using, for example, CellQuest software on a Macintosh PowerPC, or their equivalents.

Platelets are considered "activated" if they express at least 25% of the level of either P-selectin or GPIIbIIIa detected by flow cytometry on platelets treated with a final concentration of 100 μM SFLLR peptide. Platelet activation is considered "inhibited" if the level of either P-selectin or GPIIbIIIa expressed on a sample of platelets in response to 100 μM SFLLR, as measured by flow cytometry, is reduced by 25% or more in the presence of an inhibitor and SFLLR, relative to the presence of SFLLR alone.

Platelet Aggregation Assays

Platelet aggregation profiling is a standard methodology, generally performed with an instrument adapted for that express purpose, for example, a Platelet Aggregation Profiler (BioData, Horsham, Pa.). The assays can generally be performed according to the instructions of the manufacturer. As exemplary conditions, 400 μl of PRP are incubated with inhibitor for 15 minutes at room temperature. The sample is then incubated for 3 minutes at 37° C. in the Platelet Aggregation Profiler. The instrument is calibrated with platelet poor plasma serving as a blank. A baseline tracing is established by monitoring the light transmittance of PRP being stirred at 1200 rpm. Aggregation is initiated by the addition of SFLLR (200 μM) and the percent of platelet aggregation is measured by the change in light transmittance for 6 minutes following addition of SFLLR.

Platelet activation is considered "inhibited" if the percent aggregation in a sample of platelets in response to 200 μM SFLLR in an aggregation assay as described herein is reduced by 25% or more in the presence of an inhibitor and SFLLR, relative to the presence of SFLLR alone.

Animal Model of Platelet Activation, Platelet Aggregation and/or Thrombogenesis

An in vivo model of platelet activation, platelet aggregation and/or thrombogenesis provides an important tool for the analysis of new compounds, and for the optimization of individual and combination dosages of platelet-inhibiting drugs.

1. Platelet Activation.

In this animal model, a drug is administered to an animal, preferably a mammal (e.g., a mouse, rat, rabbit, dog, pig, etc.), and platelets are removed from the animal. The removed platelets are assayed for platelet activation or aggregation by one or more methods known in the art or disclosed herein. Platelet activation is "reduced" by the drug if SFLLR-induced activation, as measured by ATP release, serotonin release, or expression of P-selectin and/or GPIbIIIa, is reduced by 25% or more relative to activation measured prior to administration of the drug.

2. Platelet Aggregation.

In this animal model, a drug is administered to an animal or in (1) above, and platelets are removed from the animal. The removed platelets are assayed for platelet aggregation as known in the act or disclosed herein. Platelet activation is "reduced" by the drug if SFLLR-induced activation, as measured by ATP release, serotonin release, or expression of P-selectin and/or GPIIbIIIa, is reduced by 25% or more relative to activation measured prior to administration of the drug.

3. Intravital Animal Model for Platelet Activation, Platelet Aggregation and/or Thrombogenesis.

A preferred animal model involves intravital microscopy of laser-induced thrombi. The method is described by Rosen et al., 2001, *Am J Pathol* 158, 1613–1622, which is incorporated herein by reference. Minor variations of that method were employed as described below.

Experimental mice are pre-anesthetized and surgically prepared. A tracheal tube is placed to facilitate breathing and the jugular vein is canulated to allow for maintenance of anesthetic and introduction of compound. The cremaster muscle is then exteriorized. The muscle is affixed over a glass slide, allowing illumination from below. A steady drip of a sodium-bicarbonate buffered salt solution is maintained throughout the experiment to keep the exposed muscle moist. Blood flow in the muscle is visualized using a 40× water immersion lens and epi-illuminated with an appropriately filtered light source. Alexa 488-labeled anti-mouse CD41 antibody is injected through the jugular canulus to label platelets in vivo.

Thrombosis is initiated by damaging the vessel wall (of a 30 μm vessel) with a laser pulse from a MicroPoint LASER attached to the microscope. A LASER pulse is delivered, causing damage in an area smaller than 1 μm. The recruitment of platelets to the thrombus is then monitored by the accumulation of (activated) Alexa 488-labeled platelets at the ablation site using fluorescence microscopy, and the process is recorded digitally. The method thus permits in vivo analysis of platelet activation as measured by platelet aggregation and thrombosis.

Under these conditions, a dynamic thrombus that undergoes continuous cyclic embolization and re-accumulation is observed. The degree of embolization in an untreated mouse can be quantified using software for image analysis, e.g., BioQuant True Color Windows (Biometrics, Nashville, Tenn.), as described in Rosen et al., 2001, supra. The software package permits the determination of the "integrated optical density" or IOD of the thrombus. A 25% or greater decrease in the size of the thrombus or the degree of embolization observed at 60 seconds after injury in an animal treated with a drug, relative to the size of a thrombus or the degree of embolization at the same time after injury in an animal not receiving the drug is indicative of inhibition. Following injection of 6-(4-Amino-3-nitro-phenyl)-5-methyl-4,5-dihydro-2H-pyridazin-3-one, a thrombus formed under the same conditions shows a greater than 80% reduction of embolization. Thus, 6-(4-Amino-3-nitro-phenyl)-5-methyl-4,5-dihydro-2H-pyridazin-3-one is capable of potently inhibiting thromboembolization.

One frequent target of anti-platelet agents is phosphodiesterase III (PDE III). In order to assay whether an agent likely inhibits this enzyme, cAMP levels are measured in the presence of the agent and the agonist $PGE_1$. The assay is performed as described by Liao et al., 1998, *Eur J Pharmacol* 349,107–114, incorporated herein by reference. Briefly, aliquots of PRP are exposed to increasing concentrations of the agent for 20 minutes. The PRP is then challenged with 1 μM $PGE_1$ for 2 min The reaction is stopped by adding 10 mM EDTA, followed immediately by boiling for 2 min. The mixture is cooled to 4° C. and the precipitated protein is pelleted. cAMP content in the supernatant is quantitated using an enzyme immunoassay kit (Pharmacia-Amersham, NJ) according to the instructions of the manufacturer.

Palmitoylation Assay:

Palmitoylation can be measured according to any method known to those skilled in the art. For example, the incorporation of $^3$H-palmitate into acid-precipitable protein can be used to monitor palmitoylation. Trichloroacetic acid (TCA) precipitation, followed by scintillation counting as a means of measuring covalent protein modification, is well known to those of skill in the art.

In another approach, the fluorescence-based assay described by Varner et al. (2002, supra) can be used. The assay described by Varner et al. uses a myristoylated peptide substrate,

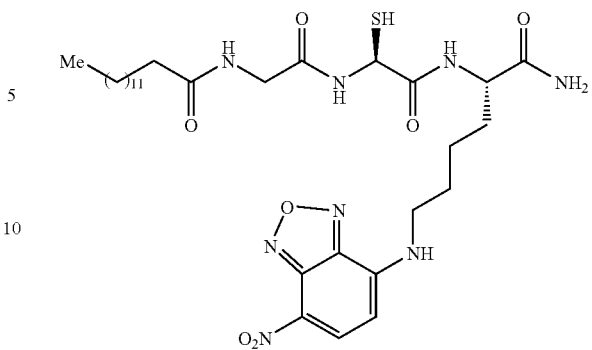

Myr-Gly-Cys, termed Myr-GCK, that mimics the palmitoylation substrate at the N-terminus of the non-receptor Src family kinases. The Myr-GCK substrate peptide and its synthesis are described by Creaser & Peterson, 2002, *J. Am. Chem. Soc.* 124: 2444–2445, which is incorporated herein by reference. The structure of the Myr-GCK substrate peptide, labeled with the NBD fluorophore NBD (7-nitrobenz-2-oxa-1,3-diazol-4-yl, available from Molecular Probes, Inc., Eugene, Ore.) is as follows:

To perform the palmitoylation assay, Myr-GCK (10 μM) fluorescently labeled with NBD is incubated for 8 minutes at 37° C. with 50 μg of protein from a cellular membrane or pellet fraction containing palmitoyl acyltransferase (see below), in acylation buffer (50 mM citrate, 50 mM phosphate, 50 mM Tris, 50 mM CAPS at pH 7.2) in a total volume of 100 μl. Palmitoyl CoA (20 μM) is then added and the mixture is incubated at 37° C. for an additional 7.5 minutes. The assay is stopped by extraction in 1.2 ml of $CH_2Cl_2$:methanol:water (2:1:1). The organic fraction is dried under $N_2$, and then analyzed by HPLC as described below.

Dried assay extracts are dissolved in 25 ml of DMSO and resolved on a reverse-phase, wide pore butyl (5 μM, 300 Å, 4.6×250 mm) HPLC column using an acetonitrile gradient with a flow rate of 1 ml/min. Initially, the mobile phase is maintained as water/50% $CH_3CN$/0.1% TFA for 5 minutes, followed by a 5 minute linear gradient from 50% to 100% acetonitrile. The mobile phase is then maintained at 100% acetonitrile for 10 minutes, followed by a linear gradient from 100% to 50% acetonitrile over 5 minutes. NBD-label is detected by fluorescence at 531 nm upon excitation at 465 nm. The percentage of palmitoylated peptide in the sample is calculated by dividing the peak area corresponding to the palmitate-modified peptide by the total peak area corresponding to both palmitoylated and un-palmitoylated peptides.

Cell fractions containing palmitoyl acyltransferase for use in the palmitoylation assay described above are prepared according to the method of Smith et al. (1995, *Mol Pharm* 47, 24 1–247), essentially as follows: Cultured cells (e.g., HepG2 or MCF-7) are grown to about 70% confluence in 150 mm tissue culture dishes and collected by centrifugation. Cells are swollen with a buffer containing 10 mM HEPES (pH 7.4), 10 mM KCl, 1.5 mM $MgCl_2$, and 5 μM PMSF for 30 minutes on ice. The cells are disrupted by homogenization and centrifuged at 5,500 g for 10 minutes at 4° C. to remove nuclei and debris. (The nuclei and debris pellet can be assayed as the pellet fraction.) The supernatant from this spin is then ultracentrifuged at 100,000 g for 1 hour at 4° C. The pellet from this centrifugation is resuspended in 100 μL of lysis buffer and collected as the membrane fraction. The supernatant is collected as the cytosolic fraction. Protein concentrations for each fraction are determined (e.g., using a fluorescamine assay, Bohlen et al., 1973, *Arch Biochem Biophys* 155, 213–220).

Platelet Inhibitory Compounds Useful According to the Invention

The invention relates to the identification of compounds as inhibitors of platelet activation. For the following, it is understood that each of the compounds disclosed and/or a pharmaceutically acceptable salt thereof can be used in a method according to the invention.

1. 9-methylene-4-(alkyl)-2,3,4,9-tetrahydro-1H-cyclopenta(b)quinolines.

The 9-methylene-4-(alkyl)-2,3,4,9-tetrahydro-1H-cyclopenta(b)quinolines, having the general structure:

wherein:

Structure 1

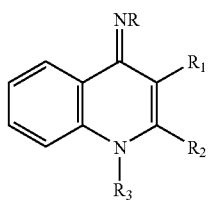

R is selected from the group consisting of H, alkyl, aralkyl, alkenyl, cycloalkyl, cycloalkenyl and substituted derivatives thereof;

$R_1$ is selected from the group consisting of H, alkyl, aralkyl, alkenyl, cycloalkyl, cycloalkenyl and substituted derivatives thereof;

$R_2$ and $R_3$ are selected from the group consisting of H, alkyl, aralkyl, alkenyl, cycloalkyl, cycloalkenyl, alkoxy or combine with the carbon atoms to form a cycloalkyl or cycloalkenyl ring and substituted derivatives thereof comprise a class of platelet inhibitors useful in the methods of the invention. For example, three such compounds, structures I-III below, potently inhibited SFLLR-induced platelet dense body and α-granule secretion and GPIIbIIIa activation, with $IC_{50}$s between 1–10 μM.

I

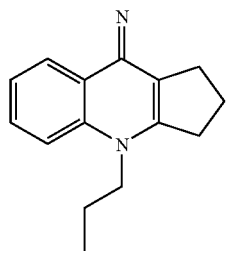

II

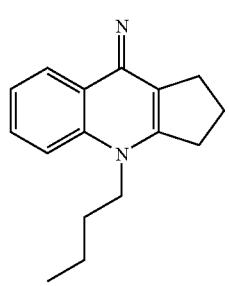

III

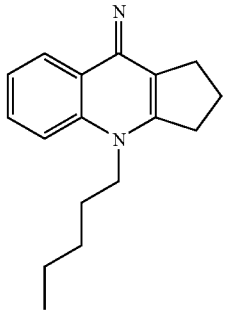

In contrast, compounds I, II and III (above) were relatively poor inhibitors of U-46619-, ADP-, and PMA-induced platelet responses. The $IC_{50}$s for inhibition of these other agonists were approximately 500 μM. Thus, there was approximately a 50-fold difference in the $IC_{50}$ of this group of compounds for inhibiting SFLLR compared with inhibition of the other agonists. The specificity of the 9-methylene-4-(alkyl)-2,3,4,9-tetrahydro-1H-cyclopenta(b)quinolines for SFLLR raised the possibility that these compounds inhibit by interacting exclusively with SFLLR. However, these compounds also inhibited activation of a 14-mer thrombin-related activator peptide with an $IC_{50}$ in the 1–10 μM range.

Compounds I, II and III above are available from ChemBridge Corporation (San Diego, Calif.), compound # 171883. Additional compounds of Structure 1 having H, alkyl, aralkyl, alkenyl, cycloalkyl, cycloalkenyl and substituted derivatives thereof at $R_1$, $R_2$ or $R_3$ can readily be generated, using chemical synthetic techniques, from these compounds or from 2,3-dihydro-1H-cyclopenta[b]quinolin-9-amine, available from, for example, Zelinsky Institute (Wilmington, Del.), Ambinter (Paris, France), and Interbioscreen Ltd. (Moscow, Russia) by those of skill in the art.

Structurally related compounds that did not have significant platelet inhibitory activity (i.e., $IC_{50}$ greater than 100 μM) are shown in FIG. 1.

The 9-methylene-4-(alkyl)-2,3,4,9-tetrahydro-1H-cyclopenta(b)quinolines only inhibit SFLLR-induced platelet activation. Distantly related platelet inhibitors, such as 9-amino-1,2,3,4-tetrahydroacridine (Liu & Sylvester,1992, Thromb Res. 67:533–544) and quinacrine (Yamakodo et al., 1984, Biochim. Biophys. Acta 801: 111–116), are not selective in that they inhibit stimulation by agonists that do not act through the thrombin receptor, such ADP, collagen, and PMA. Thus, the 9-methylene-4-(alkyl)-2,3,4,9-tetrahydro-1H-cyclopenta(b)quinolines demonstrate specificity for the most proximal events in the SFLLR-induced signaling cascade. These compounds likely act at or near the thrombin receptor. SFLLR acts through protease-activated receptor 1 (PAR1), the dominant thrombin receptor in humans (Coughlin, 2000, Nature 407: 258–264). The fact that the compounds inhibit activation by both SFLLR and a 14-mer thrombin receptor activating peptide (manuscript in preparation) demonstrates that inhibition by 9-methylene-4-(alkyl)-2,3,4,9-tetrahydro-1H-cyclopenta(b)quinolines is not an artifact of the compound binding to free SFLLR alone. Both peptides are within the activation ligand freed upon proteolytic cleavage of PAR1 by thrombin. These compounds represent a novel class of platelet inhibitors.

9-methylene-4-(alkyl)-2,3,4,9-tetrahydro-1H-cyclopenta(b)quinoline potently inhibits activation induced through the protease-activated receptor 1 (PAR1), but has little activity against activation induced through other platelet receptors, such as the thromboxane receptor, ADP receptors, or the collagen receptor(s). The compound lacks significant activity against platelet stimulation induced directly through PKC and does not inhibit phosphodiesterase. However, the compound also inhibits activation of mouse platelets by several platelet agonists. Thus, 9-methylene-4-(alkyl)-2,3,4, 9-tetrahydro-1H-cyclopenta(b)quinoline is not exclusively a PAR1 inhibitor.

In vivo studies using the intravital microscopy approach demonstrates that 9-methylene-4-(alkyl)-2,3,4,9-tetrahydro-1H-cyclopenta(b)quinoline is antithrombotic in mice. Data show that the compound is tolerated in mice. When the compound represented in Structure 1 was infused as a bolus at 6 mg/kg/5 min followed by continuous infusion at 3 mg/kg/90 min, thrombosis following laser-induced injury by greater than 80% (P<0.01). These data were obtained from 36 separate thrombi in 5 mice and demonstrate that this compound potently inhibits thrombosis in vivo.

Interestingly, 9-methylene-4-(alkyl)-2,3,4,9-tetrahydro-1H-cyclopenta(b)quinoline compounds with a longer $R_3$ group actually augment, rather than inhibit platelet activation. When $R_3$ is 3, 4 or 5 carbons long, the compound inhibits platelet activation. When $R_3$ is 6 carbons long, there is essentially no effect on platelet activation, and when compounds with $R_3$ of 7, 9, 12 and 16 carbons long were tested, they actually augmented platelet activation (data not shown).

The experimental results with the 9-methylene-4-(alkyl)-2,3,4,9-tetrahydro-1H-cyclopenta(b)quinoline compound indicate that the compound acts upon a protein that is not targeted by known anti-platelet agents. While not wishing to be bound by any specific mechanism of action, it is possible that the target of the compound is a G-Protein or a Regulator of G-Protein Signaling.

2. (1-Methyl-1-indol-3-ylmethylene)-hydrazine Carboxamines.

(1-methyl-1-indol-3-ylmethylene)-hydrazine carboxamines having the general structure

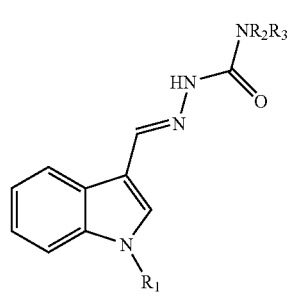

Structure 2 or a pharmaceutically acceptable salt thereof, wherein $R_1$, $R_2$, and $R_3$ are selected from the group consisting of H, alkyl, aralkyl, alkenyl, cycloalkyl, cycloalkenyl and substituted derivatives thereof, inhibit SFLLR- and U-46619-induced platelet responses. For example, the compound having the structure

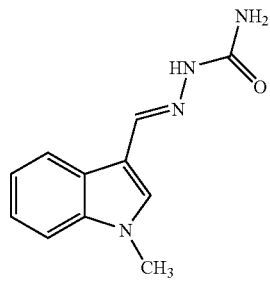

Structure 3 inhibits SFLLR- and U-46619-induced activation with an $IC_{50}$ of 20–50 µM, but has little effect on ADP- and PMA-induced activation. These compounds and the others were tested to determine whether they are likely inhibitors of phosphodiesterase, the target of a number of known platelet inhibitors. To assess their impact on phosphodiesterase activity, all compounds were assayed for the ability to augment cAMP levels upon stimulation with $PGE_1$. This analysis demonstrated that the (1-methyl-1-indol-3-ylmethylene)-hydrazine carboxamine shown above augmented cAMP levels in $PGE_1$-stimulated platelets at concentrations similar to its $IC_{50}$ for inhibition of SFLLR- and U-46619-induced platelet activation (Table III). Thus, 1-methyl-1-indol-3-ylmethylene)-hydrazine carboxamines appear to inhibit platelet activation through inhibition of phosphodiesterase.

The compound 2-[(1-methyl-1H-indol-3-yl) methylene]-hydrazinecarboxamide (Structure 3) is available from ChemBridge (#108428), Oak Samples Ltd. (Kiev, Ukraine), Otava Chemical Corp. (Kiev, Ukraine), and Interbioscreen Ltd. Those skilled in the art can readily generate compounds according to Structure 2 wherein $R_1$, $R_2$, and $R_3$ are groups including H, alkyl, aralkyl, alkenyl, cycloalkyl, cycloalkenyl and substituted derivatives thereof using the compound of Structure 3 and chemical synthetic techniques well described in the art.

3. Acetic Acid 3-(2,4-dichlorophenyl)-3-oxo-1-trichloromethyl-propyl Esters.

The acetic acid 3-(2,4-dichlorophenyl)-3-oxo-1-trichloromethyl-propyl esters having the general structure

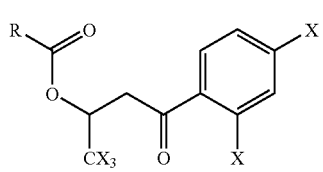

Structure 4 or a pharmaceutically acceptable salt thereof, wherein X is H or halogen and wherein $R_1$ is selected from the group consisting of H, alkyl, aralkyl, alkenyl, cycloalkyl, cycloalkenyl and substituted derivatives thereof can inhibit SFLLR- and U-46619-induced platelet responses. For example, the compound having the structure

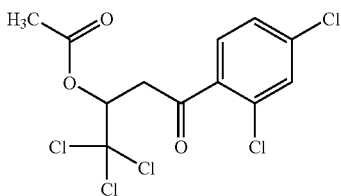

Structure 5 inhibits SFLLR- and U-46619-induced activation with an $IC_{50}$ of 20–50 μM, but demonstrates weak inhibition of ADP- and PMA-induced activation, with an $IC_{50}$ around 200 μM.

The compound of Structure 5 is available from Chembridge (#113555). Compounds having different halogens, (e.g., Br, I or F) at X or H, alkyl, aralkyl, alkenyl, cycloalkyl, cycloalkenyl and substituted derivatives thereof according to Structure 4 can be generated using chemical synthetic techniques by those skilled in the art, from the compound 3-(acetyloxy)-4,4,4-trichloro-1-(2,4-dichlorophenyl)-1-butanone, available from ChemDiv, Inc. (San Diego, Calif.), Contact Service Co. (Moscow, Russia), and Summit Pharmaceuticals International Corp. (Tokyo, Japan).

Figure 1A:
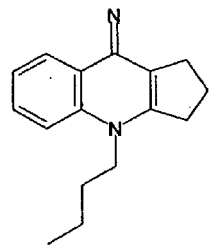
FIG. 1(a and b) shows results with compounds related to Structure 1.
Figure 1A:
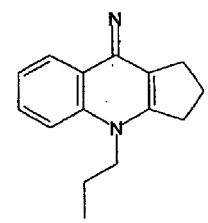
Figure 1A:
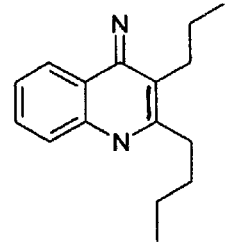
Figure 1A:
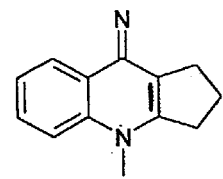
Figure 1A:
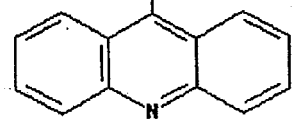
Figure 1A:
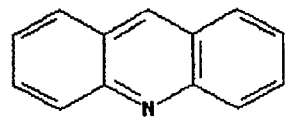
Figure 1A:
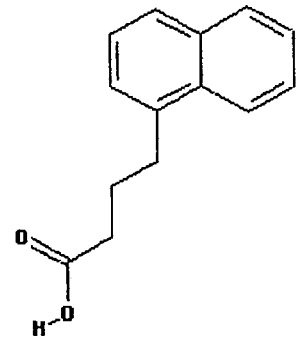
Figure 1B:
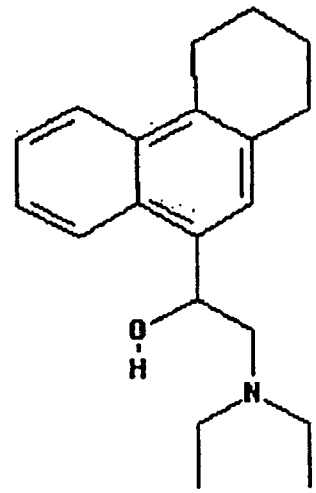
Figure 1B:
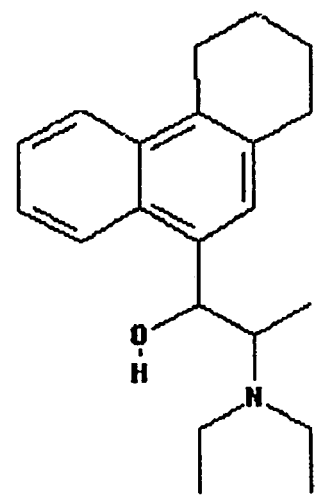
Figure 1B:
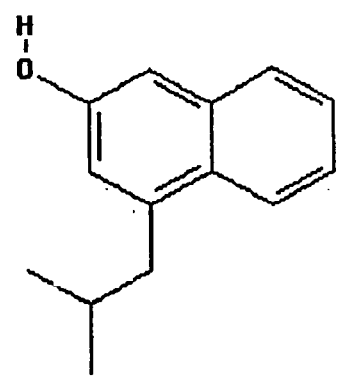
Figure 2:
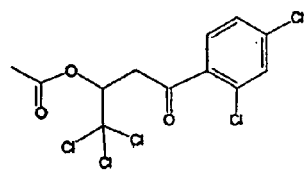
FIG. 2 shows results with compounds related to Structure 4.
Figure 2:
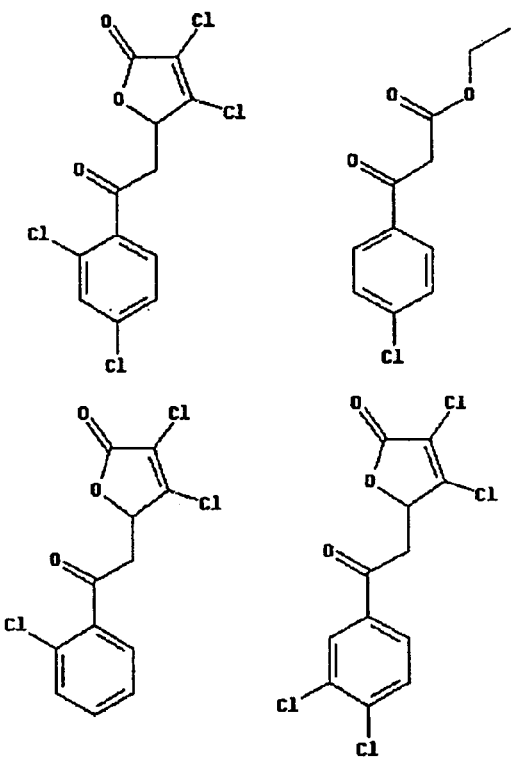

Structurally related compounds that did not have significant platelet inhibitory activity are shown in FIG. 2.

4. 6-Aryl-4,5-dihydro-3(2H)-piridazinones.

6-Aryl-4,5-dihydro-3(2H)-pyridazinones having the general structure:

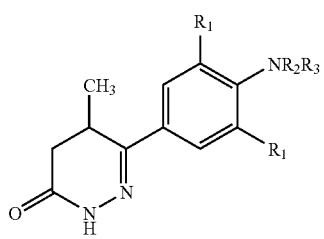

Structure 6 where $R_1$ is H or $NO_2$ and at least one of $R_1$ is $NO_2$, and where $R_2$ and $R_3$ are the same or different and are selected from the group consisting of H, alkyl, aralkyl, alkenyl, cycloalkyl, cycloalkenyl and substituted derivatives thereof, or the general structure

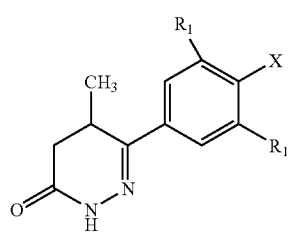

Structure 7 where $R_1$ is H or $NO_2$ and where X is halogen, were found to have strong platelet inhibitory activity. For example, the compounds of Structures 8 and 9

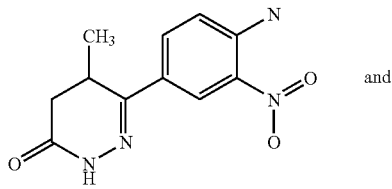

Structure 8 and

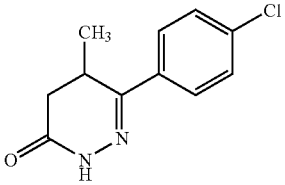

Structure 9 inhibited SFLLR and U46619-induced activation in the high nanomolar range ($IC_{50}$ for each was 0.3 μM). These compounds inhibited ADP-induced responses approximately 20-fold less effectively than they inhibited the SFLLR and U46619 responses ($IC_{50}$ of 8 μM), and they did not inhibit PMA-induced platelet activation at all.

Figure 9:
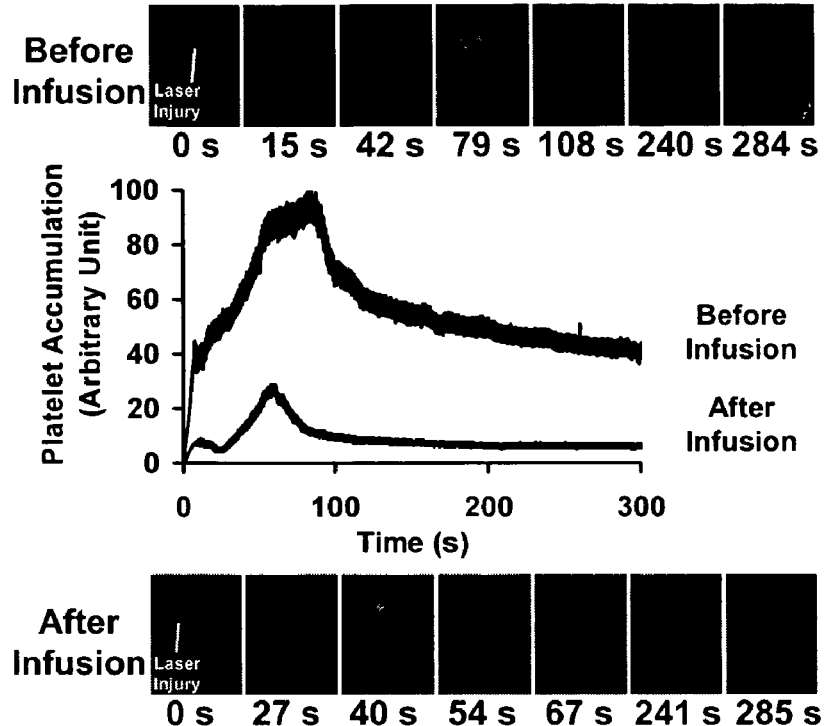
FIG. 9A–C shows the effect of PDE3 inhibition by 6-(4-amino-3-nitro-phenyl)-5-methyl-4,5-dihydro-2H-pyridazin-3-one on platelet recruitment into thrombus. (A) Platelet accumulation into thrombus before and after infusion of pyridazinone compound of a representative experiment is shown. The corresponding fluorescence microscopy images at different time points following laser injury are shown above and below the graph. The infusion of pyridazinone compound led to a significant inhibition of platelet accumulation into thrombus. (B) In the presence of 0.6 mg/kg (P<0.05) and 1.2 mg/kg (P<0.05) of pyridazinone compound, a statistically significant decrease in the maximum platelet accumulation compared to the absence of pyridazinone compound was observed. (C) A dose-dependent inhibition of the stabilized platelet accumulation was also observed in the presence of 0.6 mg/kg (P<0.05) and 1.2 mg/kg (P<0.01) of the compound. *P<005  P<0.01.
Figure 9:
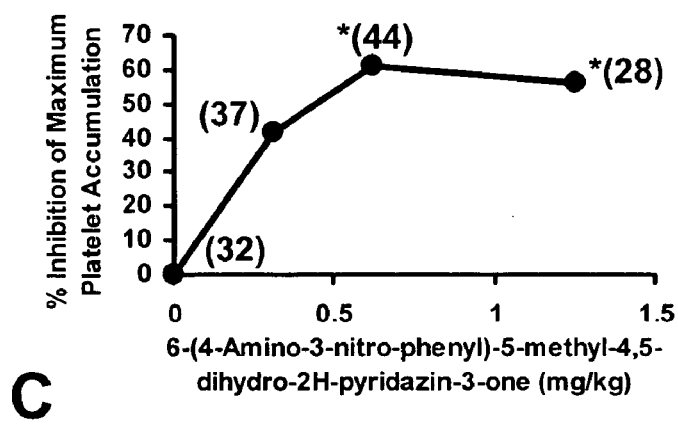
Figure 9:
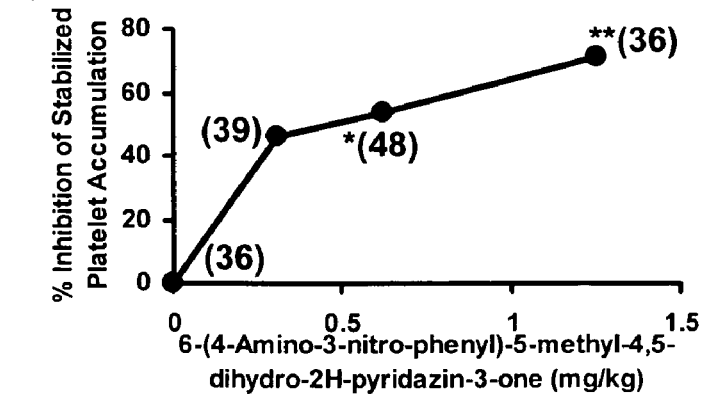
Figure 10:
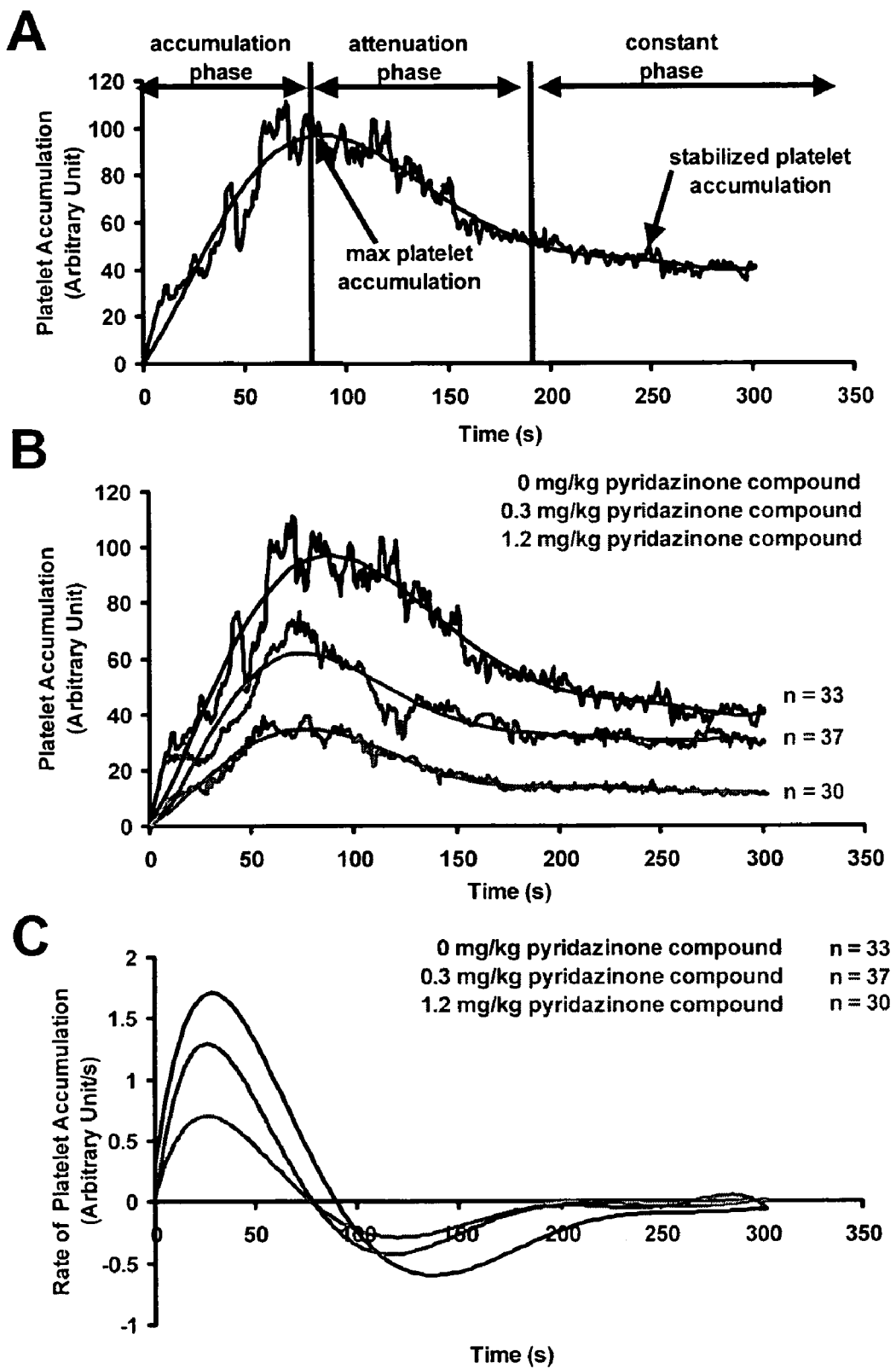
FIG. 10A–C shows kinetic analyses of platelet recruitment into thrombi following laser-induced endothelial cell injury. (A) Three phases were assigned to the dynamic process of platelet recruitment. In the accumulation phase, platelets are recruited into the growing thrombus for approximately 90 seconds until maximum platelet accumulation is achieved. In the attenuation phase, there is by a net loss of platelets from the thrombus. During the constant phase of thrombus formation, platelet content in the thrombus stabilizes. The kinetic curve was constructed based on the median value of platelet recruitment at 300 different time points of 33 independent injuries (jagged black line). A best fit curve was fitted to represent the data (smooth black line). (B) Inhibition of PDE3 activity by the infusion of either 0.3 mg/kg (green lines) or 1.2 mg/kg pyridazinone compound (pink lines) led to a decrease in maximum platelet accumulation as well as platelet accumulation in the stabilized thrombus. (C) Rate of platelet accumulation into thrombi over time in the presence of pyridazinone compound was obtained by plotting the derivative of the kinetic data illustrated in FIG. 10B. The compound was found to decrease the maximal rate of platelet accumulation without affecting the time for thrombosis to reach the maximum rate. Similarly, the compound had almost no effect on the time to maximal platelet accumulation, as indicated by point at which the rate of platelet accumulation intersects the ordinate.
Figure 11:
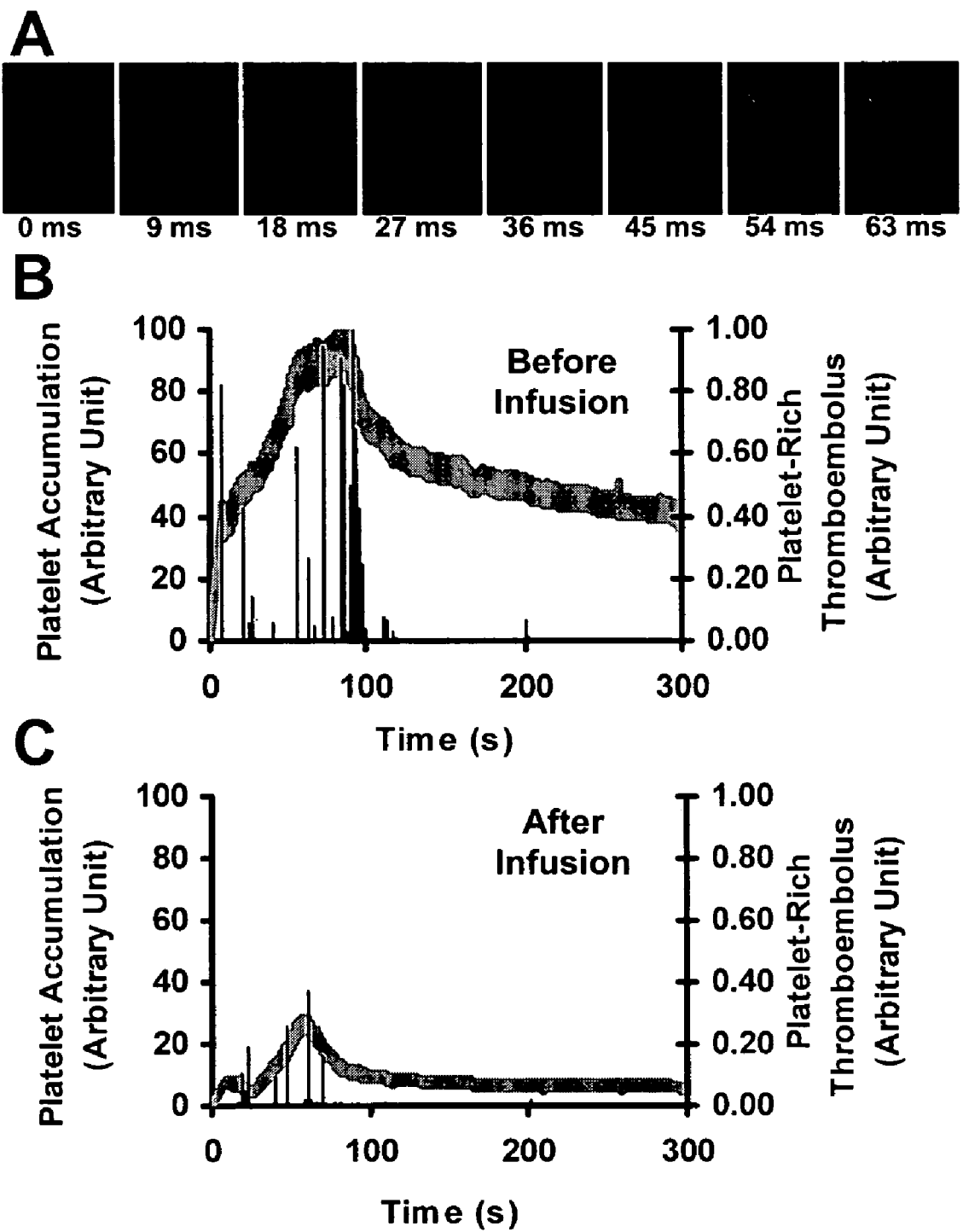
FIG. 11A–C shows data from a representative experiment for the detection of total thromboembolization before and after the infusion of pyridazione in real time.

Other pyridazinone derivatives have been found to inhibit phosphodiesterase III (PDE III; Chen et al., 1990, Zhongguo Yao Li Xue Bao 11: 338–343; Chou et al., 2000, Eur J Pharmacol. 387: 125–131; Hirose et al., 2000, Jpn. J. Pharmacol. 82: 188–198; and Hirose et al., 2000, J. Cardiovasc Pharmacol. 35: 586–594). Thus, the likely target of the 6-Aryl-4,5-dihydro-3(2H)-pyridazinone compounds is PDE III. It was therefore sought to determine the effect of the 6-Aryl-4,5-dihydro-3(2H)-pyridazinone compounds in an intravital microscopy model of laser-induced thrombosis. In this model, 6-(4-Amino-3-nitro-phenyl)-5-methyl-4,5-dihydro-2H-pyridazin-3-one inhibited thrombus formation by 72% (P<0.01; see FIG. 9). The compound also inhibited thromboembolization in the same mouse model. FIGS. 10 and 11 detail these results. This observation demonstrates that PDE III plays a role in thromboembolization. A PDE III inhibitor that is structurally unrelated to pyridazinones, termed cilostazol, recently received FDA approval for the treatment of intermittent claudication. Treatment with cilostazol increased the distance of pain free walking for patients suffering intermittent claudication by up to 59% (Beebe et al., 1999, Arch. Intern. Med. 159: 2041–2050). Because the molecular targets of cilostazol and the pyridazinone derivatives appear to be identical and the efficacy of pyridazinones in in vitro and in vivo testing is equal, if not superior, to that of cilostazol, the pyridazinone derivatives can provide a source of clinically useful anti-platelet agents.

The pyridazinones of Structures 8 and 9 are available from ChemBridge (# 144062). The 6-(4-Amino-3-nitrophenyl)-5-methyl-4,5-dihydro-5 methyl-3(2H)-pyridazinone of Structure 8 is also available from TimTec, Inc. (Wilmington, Del.), Enamine (Kiev, Ukraine), and AsInEx (Moscow, Russia). The 6-(4-chlorophenyl)-5-methyl-4,5-dihydro-5 methyl-3(2H)-pyridazinone of Structure 9 is also available from TimTec, Inc., Nanosyn Combinatorial Synthesis, Inc., Enamine, AsInEx, Aldrich Chemical Company, Inc. (Milwaukee, Wis.), and ChemDiv, Inc. Compounds having H or $NO_2$ at $R_1$ and/or H, alkyl, aralkyl, alkenyl, cycloalkyl, cycloalkenyl and substituted derivatives thereof; at $R_2$ and/or $R_3$ as in Structures 6 and 7 can be generated according to the methods described in Thyes et al., 1983, J. Med. Chem. 26: 800–807, incorporated herein by reference, combined with chemical synthetic techniques well described in the art.

5. 1-(2-Hydroxy-1,3-dioxo-indan-2-yl)-2-oxo-cyclopentanecarboxylic Acid Ethyl Esters.

1-(2-Hydroxy-1,3-dioxo-indan-2-yl)-2-oxo-cyclopentanecarboxylic acid ethyl esters having the general structure Structure 10

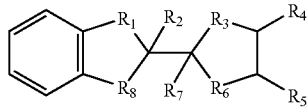

wherein: $R_1$, $R_3$, $R_6$ and $R_8$ are selected from the group consisting of $CH_2$, C=O, and $C(OR)_2$, wherein R=H, alkyl, aralkyl, alkenyl, cycloalkyl, cycloalkenyl and substituted derivatives thereof; $R_4$ and $R_5$ are selected from the group consisting of H, linear or branched alkyl, linear or branched alkenyl, or combine with the carbon atoms to which they are bonded to form a cycloalkyl or cycloalkenyl ring, aromatic ring and substituted derivatives thereof can inhibit SFLLR-, U46619- and ADP-induced platelet responses. For example, the compound having the structure Structure 11

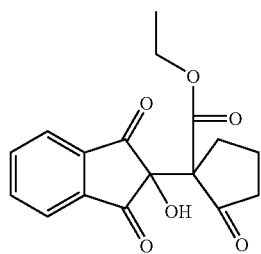

inhibits SFLLR-, U46619- and ADP-induced platelet responses (IC50 of 50 μM, 30 μM and 50 μM, respectively), but has no activity against PMA-induced responses, even at millimolar concentrations.

Figure 3:
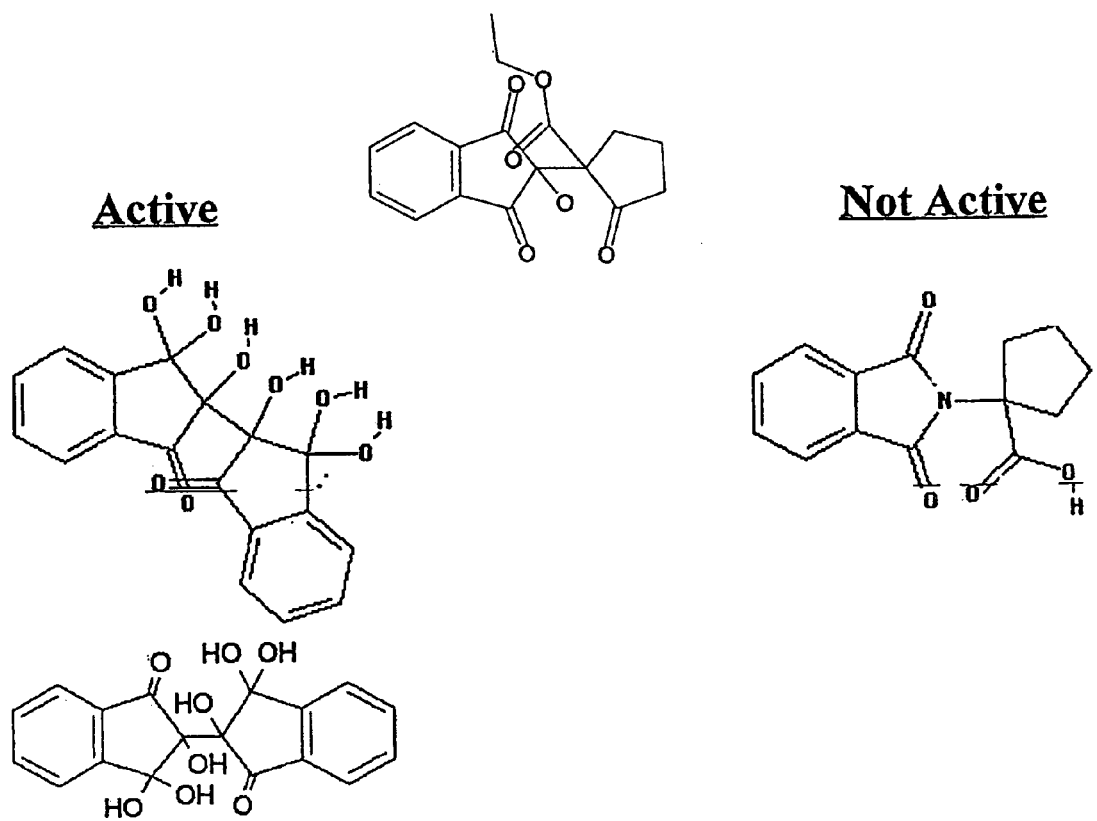
FIG. 3 shows results with compounds related to Structure 10.

A structurally related compound that did not have significant platelet inhibitory activity is shown in FIG. 3.

The compound of Structure 11 is available from ChemBridge (#115805). Compounds of Structure 10, wherein: $R_1$, $R_3$, $R_6$ and $R_8$ are $CH_2$, C=O, and $C(OR)_2$, wherein R=H, alkyl, aralkyl, alkenyl, cycloalkyl, cycloalkenyl and substituted derivatives thereof; $R_4$ and $R_5$ are selected from the group consisting of H, linear or branched alkyl, linear or branched alkenyl, or combine with the carbon atoms to which they are bonded to form a cycloalkyl or cycloalkenyl ring, aromatic ring and substituted derivatives thereof can be generated by those skilled in the art using chemical synthetic techniques and from the widely available compounds hydrindantin dihydrate or ninhydrin.

6. [1,10] Phenanthrolines.

[1,10] Phenanthroline compounds having the structure:

Structure 12

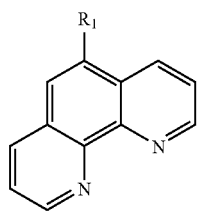

wherein $R_1$ is selected from H, alkyl, aralkyl, alkenyl, cycloalkyl, cycloalkenyl and substituted derivatives thereof, or primary, secondary, or tertiary amine, have potent anti-platelet activity. The compound [1,10] Phenanthroline-5-ylamine (Structure 13):

Structure 13

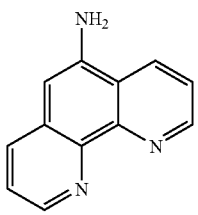

inhibits SFLLR-, U46619- and ADP-induced platelet activation ($IC_{50}$s 50 μM, 30 μM, and 50 μM, respectively), but did not inhibit PMA-induced platelet activation, even at millimolar concentrations. The compound [1,10] phenanthroline is a known chelator of iron and zinc, and has been shown to protect endothelial cells in culture, but neither [1,10] phenanthroline nor the disclosed [1,10] phenanthroline-5-ylamine compounds have been taught to have anti-platelet activity. Because the [1,10] phenanthroline-5-ylamine above failed to augment $PGE_1$-stimulated cAMP levels in in vitro assays, it is unlikely that these compounds act through elevated cAMP or phosphodiesterase inhibition.

These phenanthroline compounds and the 1-(2-Hydroxy-1,3-dioxo-indan-2-yl)-2-oxo-cyclopentanecarboxylic acid ethyl esters do not have substantial structural identity to known platelet inhibitors, but the phenotype induced by these inhibitors has been described. For example, platelets from Gαq-deficient mice fail to aggregate in response to thrombin, U-46619, ADP, and collagen, but aggregate in response to PMA (Offermans et al., 1997, Nature 389: 183–186). Thus, Gαq specifically and other G-proteins in general represent a group of potential targets for these compounds. Engagement of either SFLLR, U-46619, and ADP with its platelet receptor(s) results in activation of phospholipase C-β. It is also possible that these inhibitors act on this critical phospholipase C isoform in order to inhibit platelet activation. Alternatively, these inhibitors may act on a protein that has not previously been invoked in platelet activation. [1,10] phenanthroline-5-ylamine is of particular interest since the activity of a closely related compound, [1,10] phenanthroline, has been described in multiple biological systems. Phenanthroline is used primarily to chelate Cu2+, Fe2+, and Zn2+. It has a protective effect in cultured endothelial cells (Fratti et al., 1998, Infect. Immun. 66: 191–196; Jacob et al., 1997, Surgery 122: 243–254). It has also been shown to inhibit a platelet cGMP-inhibited phosphodiesterase (Omburo et al., 1995, Arch. Biochem. Biophys. 323: 1–5). However the $IC_{50}$ for this inhibition was approximately 2 mM. Thus, it is unlikely that [1,10] phenanthroline-5-ylamine acts through inhibition of this phosphodiesterase.

Figure 4:
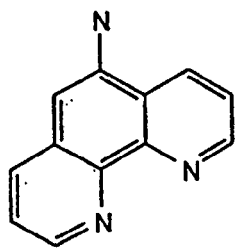
FIG. 4 shows results with compounds related to Structure 12.
Figure 4:
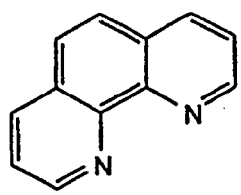
Figure 4:
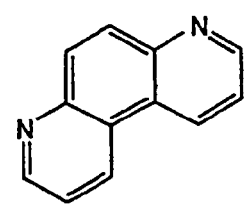
Figure 4:
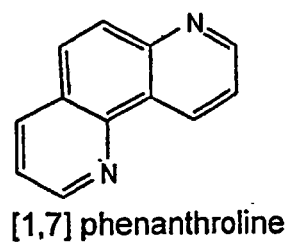
Figure 4:
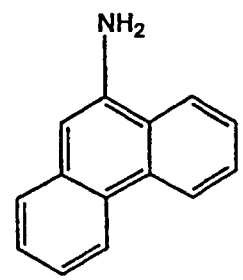
Figure 4:
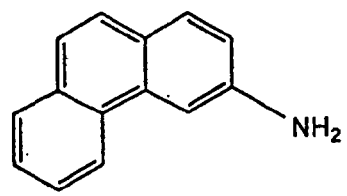

Structurally related compounds that did not have significant platelet inhibitory activity are shown in FIG. 4.

[1,10] Phenanthroline is widely available. The compound of Structure 13 is available from ChemBridge (#137237), as well as from Polysciences, Inc. (Warrington, Pa.) and City Chemical LLC (West Haven, Conn.). Compounds of Structure 12 where $R_1$ is H, alkyl, aralkyl, alkenyl, cycloalkyl, cycloalkenyl and substituted derivatives thereof, or primary, secondary, or tertiary amine can be generated by those of skill by straightforward aromatic nitration of [1,10] phenanthroline, and subsequent reduction of the nitro substituent to the corresponding amine. Further modifications according to Structure 12 can be made by those skilled in the art using standard chemical synthetic techniques.

7. Inhibitors Active On SFLLR-, U46619-, ADP- and PMA-induced Platelet Activation.

A less selective class of inhibitors was identified that was active on each of SFLLR-, U46619-, ADP- and PMA-induced platelet activation. These include the following:

a.  10H-Phenothiazine,10-(4-morpholinylacetyl)-2-(trifluormethyl).

The 10H-phenothiazine,10-(4-morpholinylacetyl)-2-(trifluormethyl) compounds with the general structure

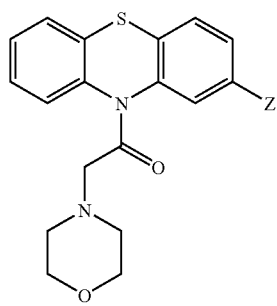

Structure 14 wherein Z can be H or $CR_1R_2R_3$, wherein $R_1$, $R_2$, and $R_3$ can be H, halogen, alkyl, aralkyl, alkenyl, cycloalkyl, cycloalkenyl and substituted derivatives thereof, also have antiplatelet activity. The compound with the structure

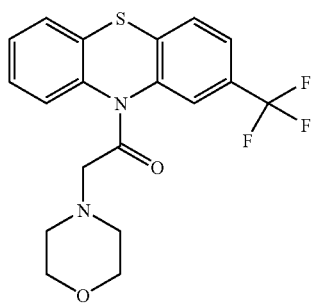

Figure 5:
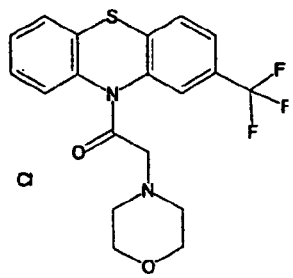
FIG. 5 shows results with compounds related to Structure 14.
Figure 5:
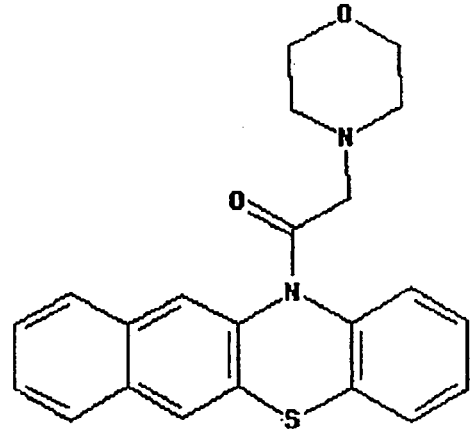

Structure 15 is active against SFLLR-, U46619-, ADP-, and PMA-induced platelet activation ($IC_{50}$s of 80 μM, 100 μM, 150 μM and 85 μM, respectively). A structurally related compound that did not have significant platelet inhibitory activity is shown in FIG. 5. Phenothiazines have previously been shown to inhibit platelet function (Kanaho et al., 1983, Thromb. Res. 31: 817–831). Phenothiazines may act through inhibition of calmodulin (White & Raynor, 1982, Biochem. Biophys. Res. Commun. 104: 1066–1072) or phospholipase C (Brufani et al., 1992, Farmaco. 47: 585–97).

Compound 15 is available from ChemBridge (#254067). Widely available phenothiazine compounds (e.g., from Rhone-Poulenc (France)) can be modified using chemical synthetic techniques by those skilled in the art to generate compounds according to Structure 14 wherein Z is H or $CR_1R_2R_3$, wherein $R_1$, $R_2$, and $R_3$ can be H, halogen, alkyl, aralkyl, alkenyl, cycloalkyl, cycloalkenyl and substituted derivatives thereof. See also Enouf & Levy-Toledano, 1984, Brit. J. Pharmacol. 81: 509–518, incorporated herein by reference, which describes multiple variants of phenothiazine compounds.

b.  2-(4-Oxo-cyclohexa-2,5-dienylideneamino)-isoindole-1,3-diones.

The 2-(4-Oxo-cyclohexa-2,5-dienylideneamino)-isoindole-1,3-dione having the structure

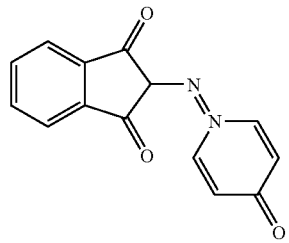

Structure 16 is active against SFLLR-, U46619-, ADP-, and PMA-induced platelet activation ($IC_{50}$s of 100 μM, 50 μM, 100 μM and 100 μM, respectively).

Figure 6:
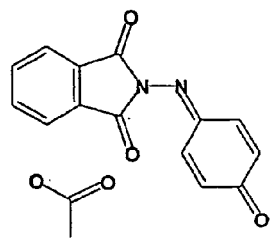
FIG. 6 shows results with compounds related to Structure 16.
Figure 6:
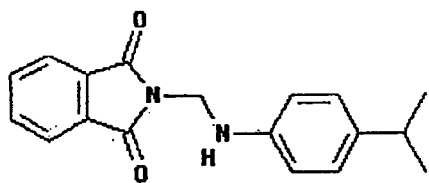
Figure 6:
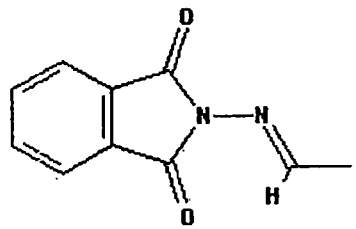
Figure 6:
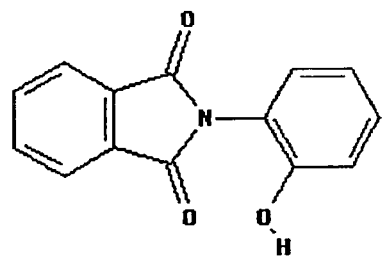
Figure 6:
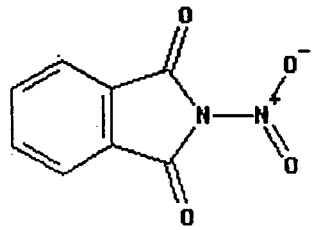

Structurally related compounds that did not have significant platelet inhibitory activity are shown in FIG. 6.

The 2-[(4-oxo-2,5-cyclohexadien-1-ylidene)amino]-1H-isoindole-1,3(2H)-dione of Structure 16 is available from ChemBridge (#133579) or from TimTec, Inc.

c.  5-Furan-2-ylmethylene-1-naphthalen-1-yl-pyrimidine-2,4,6-triones.

The 5-furan-2-ylmethylene-1-naphthalen-1-yl-pyrimidine-2,4,6-triones having the general structure

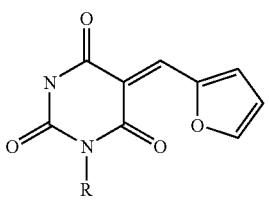

Structure 17 wherein R is aromatic, heteroaromatic, or substituents and derivatives thereof, preferably phenyl, anthracene or phenanthrene, are active against SFLLR-, U46619-, ADP-, and PMA-induced platelet activation. The compound of Structure 18: (5-(2-furanylmethylene)-1-1-naphthalenyl)-. 2,4,6(1H, 3H, 5H)-pyrimidinetrione)

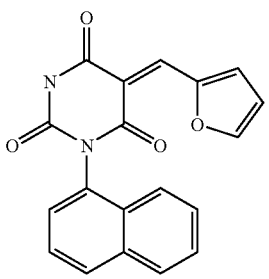

Structure 18 inhibits SFLLR-, U46619-, ADP-, and PMA-induced platelet activation with $IC_{50}$s of 100 μM, 50 μM, 60 μM and 150 μM, respectively.

Figure 7:
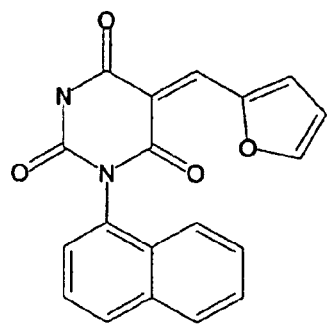
FIG. 7 shows results with compounds related to Structure 17.
Figure 7:
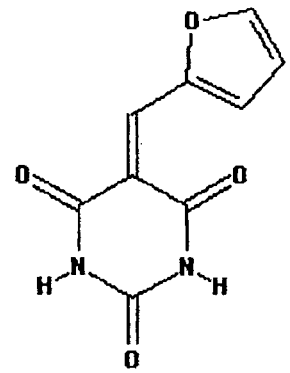
Figure 7:
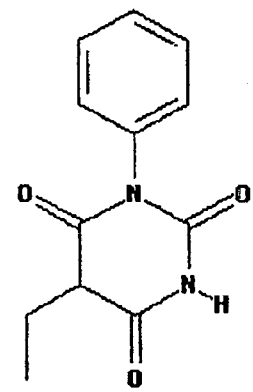

Structurally related compounds that did not have significant platelet inhibitory activity are shown in FIG. 7.

5-(2-furanylmethylene)-1-1-naphthalenyl)-2,4,6(1 H, 3H, 5H)-pyrimidinetrione is available from ChemBridge (#240683) and from Nanosyn Combinatorial Synthesis, Inc. (Mountain View, Calif.). Compounds according to Structure 17 where R is an aromatic or heteroaromatic group or a substituent or derivative thereof, can be generated from the commercially available compound 5-furan-2-ylmethylene-pyrimidine-2,4,6-trione, by aromatic substitution by those skilled in the art.

In so much as the compounds described in (a), (b) and (c) above do not show agonist specificity in the platelet assays, it is possible that these compounds act on multiple targets in the platelet. Alternatively, they may inhibit a target involved in relatively distal aspects of platelet secretion. Consistent with this hypothesis, these compounds failed to augment $PGE_1$-induced platelet cAMP levels, suggesting that they are not phosphodiesterase inhibitors. The target proteins of these inhibitors, however, are not involved exclusively in the secretory machinery since each of these inhibitors tested inhibited both GPIIbIIIa activation as well as platelet granule secretion. Certainly, protein kinase C is a possible candidate because it is stimulated by PMA and is thought to be involved in both platelet secretion (Chung et al., 2000, J. Biol. Chem. 275: 25286–25291; Sloan et al., 1997, Biochem. J. 328: 13–21) and GPIIbIIIa activation (van Willigen & Akkerman, 1991, Biochem. J. 273: 115–120).

The platelet inhibitors disclosed herein are distinguished from the oral compounds presently available in that they inhibit platelet secretion very efficiently. The presently available cyclo-oxygenase and phosphodiesterase inhibitors are significantly less potent. In addition, the platelet inhibitors disclosed herein have an advantage over drugs such as ticlopidine and clopidrogel, in that it is the molecule itself, and not an active metabolite that is active. The onset of action is thus not delayed to the extent that it is with ticlopidine and clopidrogel. This is a critical consideration in the acute treatment of myocardial infarction, unstable angina, stroke and other syndromes involving arterial thrombosis.

Dosage and Administration

The present invention provides for pharmaceutical compositions comprising a therapeutically effective amount of a platelet inhibitor as disclosed herein, in combination with a pharmaceutically acceptable carrier or excipient. The platelet inhibitors employed in the present invention can be administered by oral or parenteral routes, including intravenous, intramuscular, intraperitoneal, subcutaneous, transdermal, airway (aerosol), rectal, vaginal and topical (including buccal and sublingual) administration.

Because the platelet inhibitors useful in the invention are relatively lipophilic, oral administration is a preferred mode. For oral administration, the compounds useful in the invention will generally be provided in the form of tablets or capsules, as a powder or granules, or as an aqueous solution or suspension.

Tablets for oral use may include the active ingredients mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatin capsules in which the active ingredient is mixed with a solid diluent, and soft gelatin capsules wherein the active ingredients is mixed with water or an oil such as peanut oil, liquid paraffin or olive oil.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

For intramuscular, intraperitoneal, subcutaneous and intravenous use, the compounds of the invention will generally be provided in sterile aqueous solutions or suspensions, buffered to an appropriate pH and isotonicity. Suitable aqueous vehicles include Ringer's solution and isotonic sodium chloride. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

The compounds useful according to the invention may also be presented as liposome formulations.

In general a suitable dose will be in the range of 0.01 to 100 mg per kilogram body weight of the recipient per day, preferably in the range of 0.2 to 10 mg per kilogram body weight per day. The desired dose is preferably presented once daily, but may be dosed as two, three, four, five, six or more sub-doses administered at appropriate intervals throughout the day. These sub-doses may be administered in unit dosage forms, for example, containing 10 to 1500 mg, preferably 20 to 1000 mg, and most preferably 50 to 700 mg of active ingredient per unit dosage form.

Dosages of platelet inhibitors useful according to the invention will vary depending upon the condition to be treated or prevented and on the identity of the inhibitor being used. Estimates of effective dosages and in vivo half-lives for the individual compounds encompassed by the invention can be made on the basis of in vivo testing using an animal model, such as the mouse model described herein or an adaptation of such method to larger mammals.

In addition to their administration singly, the compounds useful according to the invention can be administered in combination with other known inhibitors of platelet activity or thrombosis. In any event, the administering physician can adjust the amount and timing of drug administration on the basis of results observed using standard measures of platelet activity known in the art or described herein.

Diseases and Gauges of Effective Treatment

The compounds useful according to the invention can be used for the treatment and/or prevention of numerous diseases or disorders involving platelet activation. In addition to known roles in disorders involving arterial thromboses, recent studies highlight a role for platelet activation and interaction with leukocytes in inflammation. This inflammation can contribute to atherosclerotic disease, as well as the pathogenesis of disorders such as allergic inflammation, asthma, inflammation accompanying wound healing, and likely any other inflammatory disorder. Therefore, the compounds useful according to the invention can also be useful for the treatment or prevention of inflammation mediated by or involving platelet activation.

1. Diseases and Disorders Involving Arterial Thrombosis.

Platelet activation is a key step in the development of arterial thrombosis. Platelet inhibitors useful according to the invention can be used to prevent or treat diseases or disorders involving arterial thrombosis. A platelet inhibitor is effective according to the invention if platelet activation or thrombus formation, is reduced by at least 10% as measured by ATP release assay, serotonin release assay, platelet aggregation assay or flow cytometry assay as described herein following administration of the inhibitor, relative to platelet activation or thrombus formation measured prior to administration.

In addition to the reduction of platelet activation as measured by the methods described herein, the efficacy of treatment or prevention of thromboses according to the invention can be assessed by monitoring the presence, severity or frequency of the symptoms. For example, when used to treat or prevent stable or unstable angina, a reduction by at least one point in the degree of chest pain reported by the patient on a scale of 1 to 10 (with 10 being the worst angina pain experienced by the patient prior to treatment) is evidence of effective treatment. Alternatively, or in addition, the frequency of pain reported by the patient can be used to monitor treatment efficacy. A reduction of 10% or more in the frequency of pain reported following treatment, relative to reports before treatment, is indicative of effective treatment. Preferably, the degree of pain or the frequency of pain or both will decrease by at least 20%, 40%, 60% 80% or more, up to and including a complete cessation of pain associated with angina. In addition to methods based on the degree or frequency of chest pain, clinical methods of monitoring unstable angina have been described. See, for example, Singh et al., 1995, *Can J Cardiol* 11, 1015–1021, incorporated herein by reference, which monitors unstable angina by evaluating the level of platelet activation-dependent microparticles in the blood by flow cytometry. Again, a decrease of 10% or more, preferably 20%, 40%, 60%, 80% or more, including 100%, in the level of platelet activation dependent microparticle, is considered to indicate effective treatment according to the invention.

When used for the treatment of acute myocardial infarction, the success of treatment can be monitored by angiography. A cardiac angiogram performed before the initiation of treatment will establish the size of one or more thrombi. Treatment is considered successful if the thrombus (or thrombi) either remains static in size (no increase) or decreases in size (e.g., by 5%, 10%, 20%, 30%, 50%, 75%, 85%, 90%, 95% or even up to and including 100%, or no thrombus) as detected by cardiac angiography after the initiation of treatment.

Cerebrovascular disease, characterized by transient ischemic attacks and strokes, can be monitored, for example, by the occurrence of microembolic signals (MES; see, for example, Serena et al., 2000, *Cerebrovasc Dis* 10, 278–82, incorporated herein by reference). Other hallmarks of cerebrovascular disease that can be monitored to assess the efficacy of treatment according to the methods of the invention include changes in motor function and changes in the size of an infarct visualized by MRI or CAT scanning. Motor function can be assessed by any of several standardized tests, such as the Minnesota Rate of Manipulation Test, or the Purdue Pegboard Test. Treatment is considered successful if motor function does not decline within 24 hours after the initiation of treatment, or if motor coordination improves (e.g., by 10%, 20%, 30%, 50%, 75%, or more) over the same time span or longer, as measured by either the Minnesota Rate of Manipulation Test or the Purdue Pegboard Test. When measuring infarct size by MRI or CAT scanning, treatment is successful if the size of the detected infarct either remains the same or decreases following the initiation of treatment.

Peripheral vascular disease (PVD) can be monitored by the level of pain reported by the patient. For example, peripheral vascular disease frequently manifests as leg pain upon exercise. Treatment for PVD is considered successful if the length of pain-free walking time of the patient increases by at least 10% following initiation of treatment, preferably by at least 20%, 30%, 50%, 75%, or more, including a doubling, tripling, quadrupling or more increase in the duration of pain-free walking. Clinical use of the pain-free walking time to assess treatment of PVD is described in Beebe et al., 1999, *Arch Intern Med* 159, 2041–2050, incorporated herein by reference.

Placental insufficiency, which involves inappropriate platelet activation, is characterized by reduced placental blood flow rate. The condition is frequently monitored by Doppler ultrasound analysis of the umbilical artery waveform, which provides a measure of the placental blood flow rate, placental blood pressure and the resistance to blood flow. Treatment of placental insufficiency with platelet inhibitors according to the invention can be monitored by following placental blood flow and/or the systolic/diastolic ratio and/or the resistance index. Doppler ultrasound analysis for placental insufficiency is well known in the art. See, for example, Galan et al., 1998, *Am J Obstet Gynecol* 178, 451–456, and Wilcox & Trudinger, 1991, *Obstet Gynecol* 77, 616–621, both of which are incorporated herein by reference.

The efficacy of treatment of placental insufficiency is evidenced by an increase in placental blood flow rate of at least 5%, and preferably at least 10%, 20%, 30%, 40% or more relative to the flow rate prior to treatment, as measured using Doppler ultrasound analysis. Similarly, a 5% or greater decrease in the resistance index, preferably a 10%, 20%, 30%, 40%, 50% or greater decrease in the resistance index is evidence of effective therapy for placental insufficiency.

Atrial fibrillation occurs in about 5% of individuals over age 65 and 10% of individuals over age 70. The arrhythmic disorder is associated with a high incidence of stroke. As a means of preventing stroke in those affected by atrial fibrillation, anticoagulant therapy is commonly prescribed. The platelet inhibitors useful according to the invention can be used in such preventive anticoagulant regimens.

The dosage of anticoagulant used in anticoagulant therapy is can be adjusted on the basis of platelet aggregation values. Aggregation of less than 50% of platelets in an aggregation assay as described herein in response to a given agonist is considered an abnormal platelet aggregation value. For preventive therapy, the dose of platelet inhibitors given can be monitored and adjusted by monitoring agonist-induced platelet aggregation in vitro before and after the initiation of treatment. The level of platelet inhibition that will be effective will vary depending upon how extreme the inappropriate platelet activity is. However a decrease of 10% or more in platelet function (preferably monitored by platelet aggregation, but possibly by other means of measuring platelet function as known in the art or described herein) will most likely have a therapeutic benefit in patients in need of preventive antithrombotic or anti-inflammatory therapy. Therefore, preventive therapy is considered successful if platelet activation is reduced by at least 10%. Ideally, platelet activation will be within the clinically accepted normal range following treatment with platelet inhibitors according to the invention. One skilled in the art can readily adjust the dosage of a given platelet inhibitor to achieve platelet activation levels within this range.

Similar platelet aggregation values could be maintained for preventive anticoagulant therapy given to patients undergoing surgical procedures with an increased risk of thromboses, including, for example, aortocoronary bypass surgery, coronary angioplasty or stent placement, and insertion of prosthetic heart valves. When platelet inhibitors useful according to the invention are used to prevent or reduce the likelihood of thromboses associated with surgical procedures, their effectiveness can also be monitored by, for example, Doppler ultrasound to monitor the continued flow rate of blood through the affected region. A means particularly well suited to monitoring thromboses associated with heart valve replacement is echocardiography. The technique, which permits the visualization of thromboses, is useful to determine whether a thrombus is remaining static in size (no increase) or shrinking relative to the size before the initiation of treatment, both of which are hallmarks of successful anticoagulant treatment.

Platelet inhibitor compounds useful according to the invention can be used to reduce or prevent inflammation. Among the hallmarks of local acute inflammation are heat, redness, swelling, pain and loss of function. These changes are induced largely by changes in vascular flow and caliber, changes in vascular permeability and leukocyte exudation (Robbins et al., "Pathologic Basis of Disease", 6$^{th}$ Ed., W. B. Saunders Co., Philadelphia, Pa.). Anti-inflammatory therapy performed using compounds useful according to the invention can be monitored for success by tracking any of these changes. For example, a decrease in swelling (e.g., at least 10% decrease following treatment) or reported pain (e.g., a sustained decrease of 1 point or more on a 1–10 scale reported by the patient, with 10 being the worst pain experienced in association with this disorder prior to treatment, and 0 being no pain) can be used to indicate successful treatment.

Other measurable hallmarks of inflammation include leukocyte infiltration and inflammatory cytokine levels. These hallmarks can be monitored by biopsy of the affected tissue. A decrease of 10% or more in leukocyte infiltration in fixed, stained tissue relative to infiltration in similar tissue prior to treatment can be used to indicate successful treatment, as can a decrease of 10% or more in the level of any given inflammatory cytokine, relative to the level before treatment. Those skilled in the art can readily assay for inflammatory cytokine levels in tissue or blood samples. Alternatively, the level of systemic indicators of inflammation such as C reactive protein levels and erythrocyte sedimentation rate can be monitored. Each of these has established normal ranges in medicine, and treatment is considered successful if one or more of such indicators goes from outside the normal range to inside the normal range after the initiation of treatment.

EXAMPLES

Example 1

Effect of Compounds Useful According to the Invention on Agonist-induced Platelet Activation Compounds were tested for the ability to inhibit agonist-induced ADP/ATP release from platelet dense granules using a luciferin-luciferase reporter system. In this assay, compounds were incubated with platelet-rich plasma (PRP) for 30 min. A cocktail of the platelet agonist and luciferin-luciferase was then added to the wells. Plates were immediately analyzed using a Tundra high density luminescence imager. This assay demonstrated a signal to noise ratio of greater than 100:1. As a control, compounds were also screened in a platelet-free assay for the ability to inhibit luciferin-luciferase upon exposure to ATP.

Each of the compounds was tested for inhibition of platelet activation in response to the agonists SFLLR (a thrombin mimic), U46619 (a thromboxane A2 mimic), ADP and the phorbol ester PMA.

Example 2

Effect of Compounds Useful According to the Invention on GPIIbIIIa Activation

Compounds were also tested by flow cytometry for the inhibition of SFLLR-induced GPIIbIIIa activation and P-selectin expression. In these experiments, freshly obtained PRP was prepared from healthy volunteers who had not ingested aspirin for two weeks prior to donation. Forty μl of PRP was incubated with inhibitor in DMSO or DMSO alone for 15 min. The sample was then incubated with the indicated agonist for 10 min. Following incubation of the sample with the indicated agonist, 10 μl of reaction mixture was transferred to 5 μl of PE-conjugated AC1.2 anti-P-selectin antibody (for assessment of P-selectin surface expression) or FITC-conjugated PAC-1 antibody (for assessment of GPIIbIIIa activation). PBS (500 μl) was added to the sample after a 20 min incubation and the platelets were analyzed immediately by flow cytometry. Flow cytometry was performed using a Becton-Dickinson FACSCalibur flow cytometer. Fluorescent channels were set at logarithmic gain. Ten thousand particles were acquired for each sample. A 530/30 band pass filter was used for FL-1 fluorescence. A 585/42 band pass filter was used for FL-2 fluorescence. FITC was measured in the FL-1 channel and PE was measured in the FL-2 channel. Data were analyzed using CellQuest software on a MacIntosh PowerPC. Table I shows the effect of the inhibitors on platelet activation as measured by P-selectin expression. Results for GPIIbIIIa activation are shown in Table II.

Example 3

Augmentation of $PGE_1$-induced cAMP Levels in Platelets by Inhibitors Useful According to the Invention In order to assess whether the compounds useful according to the invention might act through inhibition phosphodiesterase III, each was tested for its effect on $PGE_1$-induced cAMP increase. Determination of platelet cAMP levels was performed as described by Liao et al., 1998, supra. Aliquots of PRP were exposed to increasing concentrations of the indicated compounds for 20 min. PRP was then challenged with 1 µM PGE$_1$ for 2 min. The reaction was stopped with the addition of 10 mM EDTA followed immediately by boiling for 2 min. The mixture was then cooled to 4° C. and the precipitated protein was pelleted. Cyclic AMP content in the supernatant was then quantified using an enzyme immunoassay kit (Pharmacia-Amersham, NJ) according to the instructions of the manufacturer. Results are shown in Table III.

Example

4. Detailed analysis of anti-thrombotic activity of 6-(4-Amino-3-nitro-phenyl)-5-methyl-4,5-dihydro-2H-pyridazin-3-one.

A. Characterization of anti-platelet activity.

The pyridazinone compound 6-(4-Amino-3-nitro-phenyl)-5-methyl-4,5-dihydro-2H-pyridazin-3-one was assessed for its inhibitory effect on a variety of agonist-induced platelet functions. Compound was tested for its ability to inhibit SFLLR-, U46619-, ADP-, PMA-, and collagen I-induced platelet α-granule secretion. In these assays, platelets were incubated with increasing doses of compound for 30 minutes. The platelets were then exposed to a maximally stimulatory dose of the indicated agonist. P-selectin surface expression was analyzed by flow cytometry using phycoerythrin-anti-P-selectin to monitor for α-granule secretion. The IC$_{50}$s for the ability of compound to inhibit platelet α-granule secretion induced by the indicated agonist is shown in FIG. 8A.

In agreement with the experiments in Examples 1 and 2, the compound was found to inhibit SFLLR- and U46619-induced human platelet alpha-granules release with an IC$_{50}$ of 0.3 µM as monitored by P-selectin expression using flow cytometry. In contrast, the IC$_{50}$s for ADP (8 µM)- and collagen-induced platelet granule release (70 µM) were at least 25-fold less potent. No inhibition of PMA-induced activation was observed up to 1000 µM. Therefore, this pyridazinone compound exhibited selective inhibition of agonist-induced platelet α-granule secretion.

To determine whether or not the effects of the pyridazinone compound were limited to inhibition of alpha-granule secretion, the ability of the compound to inhibit F-actin assembly and a$_{IIb}$β$_3$ activation was examined. F-actin assembly was detected using FITC-phalloidin and quantified by flow cytometry (Winokur et al., 1995, *Blood* 85, 1796–804; Oda et al., 1992, *Blood* 79, 920–7).

Figure 8:
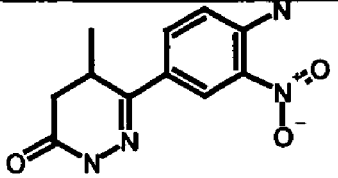
FIG. 8A–C shows the results of in vitro characterization of 6-(4-amino-3-nitro-phenyl)-5-methyl-4,5-dihydro-2H-pyridazin-3-one. (A) Compound was tested for its ability to inhibit SFLLR-, U46619-, ADP-, PMA-, and collagen I-induced platelet α-granule secretion. (B) The effect of the compound on $PGE_1$-stimulated cAMP elevation was analyzed. Platelets were incubated with increasing doses of pyridazinone compound for 30 minutes prior to the 2 minute incubation with $PGE_1$. Platelets were subsequently lysed and cAMP level was assayed using a commercially available ELISA kit (Liao et al., 1998, *Eur J Pharmacol* 349, 107–14). Pyridazinone compound was found to augment $PGE_1$-induced cAMP level increase in platelets in a dose-dependent manner. Error bars represent mean ±1 SD (n=4), *P<0.001. (C) Pyridazinone compound was found to inhibit human platelet PDE3 with an $IC_{50}$ of 15 nM. No significant inhibition of human recombinant PDE2 and human platelet PDE5 was detected.
Figure 8:
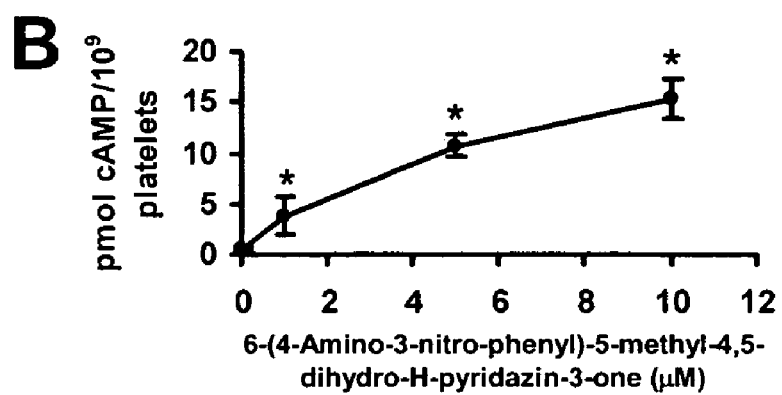
Figure 8:
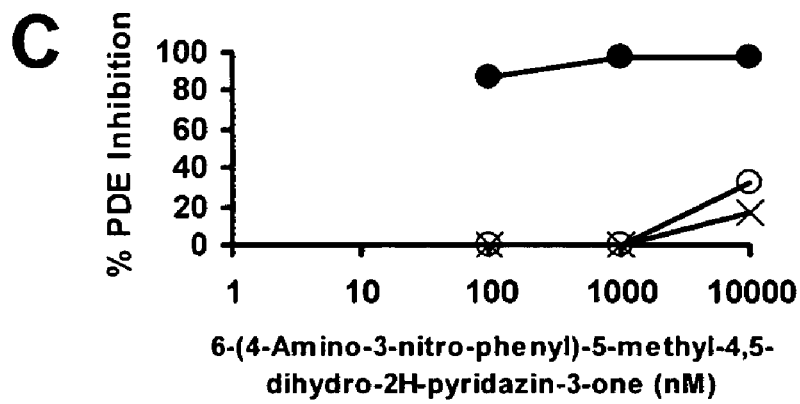

Experiments on F-actin assembly showed that this compound interferes with SFLLR-induced cytoskeleton rearrangement (FIG. 8A). SFLLR-induced α$_{IIb}$β$_3$ activation, measured using PAC-1 antibodies, was also inhibited by this compound (FIG. 8A). Platelet aggregometry studies showed that this compound is a potent inhibitor of SFLLR-induced platelet aggregation. The potency of the compound for inhibiting aggregation is similar to that for inhibiting P-selectin expression and α$_{IIb}$β$_3$ activation (data not shown). Inhibition of SFLLR and U46619 but not PMA indicates that this compound targets signaling pathways upstream to protein kinase C.

B. Investigation of PDE3-inhibitory activity of 6-(4-Amino-3-nitro-phenyl)-5-methyl-4,5-dihydro-2H-pyridazin-3-one.

The experiments described in Example 3 show that 6-(4-Amino-3-nitro-phenyl)-5-methyl-4,5-dihydro-2H-pyridazin-3-one augments PGE$_1$-induced cAMP levels in a dose-dependent manner (FIG. 8B). Intracellular cAMP generated by adenylyl cyclase in platelets is actively hydrolyzed by phosphodiesterase. The increase in cAMP in the presence of pyridazinone compound upon stimulation by PGE$_1$ demonstrates that this compound is a phosphodiesterase (PDE) inhibitor. Human platelets express PDE2, PDE3, and PDE5. Therefore, the compound was tested for its inhibitory effect on these phosphodiesterases using methods as described in Example 3. The pyridazinone compound inhibited human platelet PDE3 with an IC$_{50}$ of 15 nM (see solid circles in FIG. 8C). In contrast, the compound demonstrated little inhibition of recombinant human PDE2 or human platelet PDE5 up to 1 µM (FIG. 8C, open circles and "x"). These results demonstrate that this compound is a highly selective PDE3 inhibitor.

C. Effect of PDE3 inhibition on platelet recruitment.

PDE3 functions to decrease the amount intracellular cAMP, which serves to activate protein kinase A (PKA). Some of the intracellular substrates that are phosphorylated by PKA include IP$_3$ receptor and Gα$_{13}$, which play roles in the down-regulation of calcium release and inhibition of RhoA/Rho kinase pathway, respectively. GPIbβ is also one of the substrates of PKA. The phosphorylation of GPIbβ may cause inhibition of collagen-induced actin polymerization. PDE3 also negatively regulates PKA phosphorylation of cytoskeleton proteins such as actin binding protein and caldesmon, which may stabilize resting platelet cytoskeleton. Thus, PDE3 phosphodiesterase activity down-regulates the PKA inhibitory effect on platelet activation. A role for PDE3 in thrombus formation has been suggested in both in vivo models and in clinical studies of arterial thrombosis. However, the effects of PDE3 inhibition on platelet recruitment into thrombi have not been examined until now.

Using quantitative intravital fluorescence videomicroscopy with high temporal resolution (111 images/second), the effect of PDE3 inhibition on the platelet recruitment into thrombi was directly observed over time. Platelets were fluorescently labeled by infusing rat-anti-mouse CD41 and Alexa 488-anti-rat IgG through a cannulated jugular vein. The cremaster microvasculature was exposed and mapped and suitable arteriole segments were selected for laser-induced injury. A series of control injuries were generated prior to infusion of the inhibitory compound. The power and the number of laser pulses required to generate each thrombus was recorded. Platelet accumulation to the thrombi following laser ablation was recorded using digital videomicroscopy. The thrombus total fluorescence in each frame of the videos was analyzed using Slidebook software for digital videomicroscopy. The pyridazinone compound was then infused. Following a 15 minute incubation, a series of experimental injuries were generated 250 µm proximal, with relationship to blood flow, of the first injury and the resultant thrombi were recorded. The power and the number of pulses required to induce the control thrombus was used to induce the experimental thrombus. The control and experimental thrombi constituting a pair were compared for statistical analysis. The total fluorescence intensity of the thrombi before and after the infusion of pyridazinone compound was recorded.

Images from a representative experiment of the recruitment of fluorescently-labeled 30 platelets into a growing thrombus over time is shown in FIG. 9A. The inhibition of PDE3 by the pyridazinone compound led to a significant inhibition of platelet accumulation into thrombus. The anti-thrombotic effect of PDE3 inhibition on the maximum platelet accumulation and the stabilized platelet accumulation 300 seconds after the laser injury was quantified. The maximum platelet accumulation was measured by determining the value representing the highest total fluorescence observed for each thrombus and the stabilized platelet accumulation was determined by the value representing the fluorescence at which the thrombus remained constant over time following laser ablation. A dose-dependent inhibition of the maximum platelet accumulation was observed. In the presence of 0.6 and 1.2 mg/kg of compound, maximum platelet accumulation was inhibited by 61% (n=44) and 56% (n=8) respectively, a statistically significant inhibition compared to the absence of the compound (FIG. 9B). A statistically significant dose-dependent inhibition of the stabilized platelet accumulation was also observed. In the presence of 0.6 mg/kg and 1.2 mg/kg of the compound, stabilized platelet accumulation was inhibited by 54% (n=48) and 72% (n=36) respectively (FIG. 9C). These results show that PDE3 affects the recruitment of platelets into thrombi in a dose-dependent manner.

D. Use of 6-(4-Amino-3-nitro-phenyl)-5-methyl-4,5-dihydro-2H-pyridazin-3-one to examine the kinetics of thrombosis in vivo.

Platelet accumulation during thrombus formation is the initial step in the development of a stable thrombus in response to endothelial cell injury. Platelet accumulation is controlled by the degree and the rate of platelet recruitment. In this mouse model, platelet accumulation to thrombi occurs in a specific temporal pattern in which the amount of platelet accumulation varies over time (FIG. 9A). Using the time course data recorded for the thrombi in the experiments above, a composite kinetic profile was generated to examine the dynamics of the thrombotic process. The time course of thrombus formation based on the median platelet accumulation of 300 time points of 33 laser injuries is shown in FIG. 10A. Three distinct phases of platelet recruitment following laser-induced endothelial injury can be assigned. In the accumulation phase immediately following laser injury, platelets are recruited into the growing thrombus for approximately 90 seconds until maximum platelet accumulation is achieved. The subsequent attenuation phase is characterized by a net loss of platelets from the thrombus. During the constant phase of thrombus formation, platelet content in the thrombus stabilized. A dose-dependent effect of the pyridazinone compound on the kinetics of thrombosis was observed (FIG. 10B). When mice were infused with 0.3 mg/kg and 1.2 mg/kg of the compound, the maximum platelet accumulation, the stabilized platelet accumulation, as well as the platelet accumulation at each time point was inhibited. These results demonstrate that this compound is a potent anti-thrombotic. Although PDE3 inhibition reduced platelet accumulation into thrombus, the discrete temporal pattern of the different phases in thrombosis is preserved and the kinetic profile of platelet recruitment to thrombi is maintained. The rate of platelet recruitment into thrombus over time was analyzed by determining the derivative of the kinetic data in FIG. 10B. Several aspects of PDE3 inhibition by the compound on the rate of platelet recruitment were observed (FIG. 10C). In the presence of 0.3 mg/kg and 1.2 mg/kg of the pyridazinone compound, the maximal rate of platelet recruitment was inhibited by 37% and 56% respectively. Although inhibition of PDE3 affected the maximal rate of platelet recruitment, PDE3 inhibition did not affect the time it took to achieve the maximum rate, which was attained approximately 27 seconds after the laser injury. Also, changes in PDE3 activity had almost no effect on the time to maximal platelet accumulation, as indicated by the point at which the rate of platelet recruitment intersects the ordinate. These data demonstrate that the PDE3 directly modulates specific aspects of thrombus formation such as maximal platelet recruitment while leaving other aspects of thrombus formation such as time to maximum recruitment rate or time to maximum platelet accumulation unchanged. Thus, kinetic analysis of platelet recruitment to thrombi reveals PDE3-sensitive and PDE3-insensitive aspects of platelet accumulation during thrombus formation. Time to maximum rate or time to maximum platelet accumulation may require aspects of platelet function not dependent on PDE3 activity, such as vWF-GPIb or collagen-GPVI adhesion interactions, while platelet accumulation is dictated by factors that are inhibited by the compound, such as platelet secretion or activation of $\alpha_{IIb}\beta_3$, which result from signal transduction events subsequent to engagement of platelet surface receptors.

E. Investigation of platelet loss after reaching the point of maximum platelet accumulation.

One prominent feature of the kinetics of platelet recruitment in the in vivo model is that there is a loss of platelets from the thrombus following the point of maximal platelet accumulation. To investigate whether the net decrease in platelet content after a thrombus reached its maximum platelet accumulation is a regulated or random process, correlation between the stabilized platelet accumulation and the maximum platelet accumulation was examined. A strong correlation between the stabilized platelet accumulation and the maximum platelet accumulation was revealed (Table IV). A statistically significant correlation was observed for the saline group with a correlation coefficient of 0.88 and P-value<0.0005. Significant correlations were also observed when thrombi were formed in the presence of each of the different concentrations of the pyridazinone compound. Median stabilized platelet accumulation ranged from 33% to 41% of the maximum platelet accumulation in the presence of different amounts of pyridazinone compound. These results show that the formation of the thrombus and the subsequent reduction in platelet content are tightly regulated. Although the maximum platelet accumulation and stabilized platelet accumulation are both sensitive to PDE3 activity, inhibition of PDE3 does not disrupt the coordinated events that direct the relationship between maximum platelet accumulation and stabilized platelet accumulation.

F. Quantitation of thromboemboli.

The mechanism whereby platelets are lost following maximal platelet accumulation to thrombi is unknown. During the course of thrombus development, visible platelet-containing thromboemboli of different sizes originated from the thrombus. The percentage of adherent platelets that were lost via thromboembolization following maximal platelet accumulation was therefore examined. Previously reported methods of studying thromboembolism include monitoring the number of thromboemboli and the duration of thromboembolism after vessel wall puncture (Broeders et al., 1998, *Arterioscler Thromb Vasc Biol* 18, 139–45; oude Egbrink et al., 1993, *Thromb Haemost* 70, 826–33; and oude Egbrink et al., 1988, *Thromb Haemost* 59, 23–8) and laser-induced injury (Nagamatsu et al., 1999, *Clin Lab Haematol* 21, 33–40 and Aguejouf et al., 2000, *Thromb Res* 99, 595–602) as well as survival studies of mice challenged with injection of different platelet agonists (H. Ma et al., 2001, *Circulation* 104, 1176–80, and Hirsch et al., 2001, *Faseb J* 115, 2019–21). Those studies have shown that inhibition of thrombosis leads to a concomitant reduction in the number of thromboemboli, the duration of thromboembolization, as well as increased survival rate upon thromboembolism induction. However, the methods used in those studies do not permit the quantitation of the total mass of thromboemboli that originates from a thrombus as a percentage of maximum platelet accumulation.

Using quantitative intravital fluorescence videomicroscopy with high temporal resolution, thromboemboli were detected and the total amount of fluorescence of the thromboemboli was measured (FIG. 11A). For this analysis, thromboembolus was defined as a platelet aggregate with a fluorescent intensity two standard deviations above the maximum background fluorescence of the arteriole before injury. The total amount of thromboemboli resulting from a thrombus was normalized and expressed in terms of percent of maximum platelet accumulation of the same thrombus. Thromboembolization over time was analyzed together with thrombi formation in the absence (FIG. 11B) or presence (FIG. 11C) of the infusion of 1.2 mg/kg pyridazinone. The median total thromboembolization in the absence of pyridazinone compound was 3.5% (n=33) of the maximum platelet accumulation. In comparison, the net change between the maximum platelet accumulation and stabilized platelet accumulation of mice infused with saline was 66% (Table IV). Therefore, visible thromboembolism detectable by high speed videomicroscopic technique constituted only a small fraction of the net change observed in platelet accumulation and was not a major mechanism contributing to the reduction of platelet accumulation over time. In the presence of 1.2 mg/kg pyridazinone compound, the median total thromboembolization was 1.0% (n=3 1) of the maximum platelet accumulation of control thrombi (p<0.04). Thus, the elevation of platelet intracellular cAMP resulting from the inhibition of PDE3 led to a significant decrease in thromboembolization. Thus, while thromboembolization is not responsible for the majority of loss of platelets in the attenuation phase, thrombembolism is under control of PDE3.

In these studies, thromboembolization was observed to occur during the accumulation phase before the thrombus reached its maximum platelet accumulation as well as in the attenuation phase (FIG. 11). Net platelet accumulation into a thrombus is, thus, a dynamic process wherein recruitment of platelets occurs simultaneously with loss of platelets. The mechanism of loss of the majority of platelet mass during the attenuation phase is likely to result from the detachment of platelet microaggregates or individual platelets that cannot be detected even by videomicroscopy with high temporal resolution. Fibrinolysis and shear force may also contribute to the loss in platelet mass during the attenuation phase.

In this study, use of intravital digital videomicroscopy has permitted the definition of three distinct phases of platelet recruitment following laser-induced endothelial injury. The phases include an accumulation phase, an attenuation phase, and a constant phase. The use of a pyridazinone compound of the invention as a novel molecular probe that potently inhibits in vitro platelet activation by inhibiting PDE3 has permitted the determination of PDE3-sensitive and PDE3-insensitive aspects of the accumulation phase. Intravital digital videomicroscopy has also enabled the evaluation of the role of thrombembolism in the attenuation phase, demonstrating that thromboembolism accounts for only a small fraction of the loss of platelet mass. The observation of thromboembolization during the accumulation phase shows that the total platelet content in a thrombus at any time point is likely to be the net accumulation of platelets under the two opposing dynamic processes of platelet recruitment and platelet detachment. These studies support a model whereby overall platelet accumulation into thrombus is determined by changes in the rate of recruitment and the rate of detachment, which are controlled, in part, by platelet PDE3 activity.

Example 5

Identification of Palmitoylation As A Target For Inhibiting Thrombus In Vivo.

Three of the compounds identified by high throughput screening were found to belong to the same family, differing in structure only by the number of carbon in their alkyl chain. The structures are shown below and in FIG. 12:

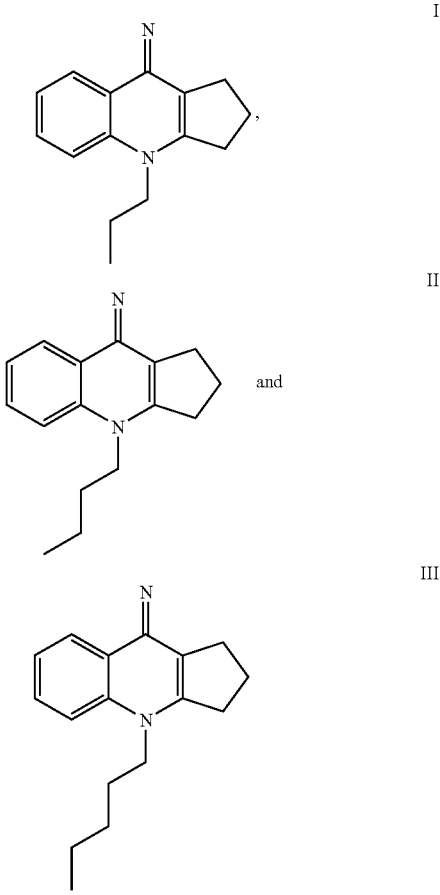

These 9-methylene-4-(alkyl)-2,3,4,9-tetrahydro-1H-cyclopenta (b) quinoline compounds were termed JF081204 and were named with a suffix indicating the length of their alkyl chain. For example, {5C} denotes a 5-carbon alkyl tail. JF081204{5C}, JF081204{4C}, and JF081204{3C} were found to have $IC_{50}$s ranging from 2 to 150 μM in SFLLRN-induced P-selectin expression assays using flow cytometry. These results suggest that activity of the compound is correlated to the length of the alkyl chain.

In vitro characterization of inhibitors of platelet activation

Ten structural analogs of the JF081204 family that differed only in the length of their alkyl tail were examined to further elucidate the role of the length of the alkyl chain of these compounds in platelet activation. At 30 μM, JF081204 compounds with a 4- or 5-carbon chain, but not with a shorter or longer carbon chain, inhibited platelet activation stimulated by a maximal dose of 200 μM SFLLRN (FIG.

13). Interestingly, JF081204 compounds with 7-carbon or longer chain augmented P-selectin expression in the presence of a submaximal dose of 20 µM SFLLRN. This augmentation was SFLLRN activation-dependent because JF081204{7C}, {9C}, {12C}, and {16C} by themselves did not activate platelets in the absence of SFLLRN (FIG. 13). Overall, these JF081204 analogs demonstrated that the length of the alkyl chain of the compounds is a critical determinant of their activities.

JF081204{5C}, which exhibited the strongest inhibitory effect on platelet activation, was assessed for its inhibitory effect on a variety agonist-induced platelet functions (Table V). The compound was found to inhibit SFLLR-induced P-selectin expression on human platelets with an $IC_{50}$ of 2 µM using flow cytometry. In contrast, the $IC_{50}$s for U46619-, A23187-, and PMA-induced P-selectin expression were at least 150 fold-less potent. Platelet aggregometry studies showed that JF081204{5C} was a potent inhibitor of SFLLRN- and epinephrine-induced platelet aggregation with $IC_{50}$ of under 5 µM. However, it was not effective in inhibiting U46619-, and collagen-induced platelet aggregation.

Figure 14:
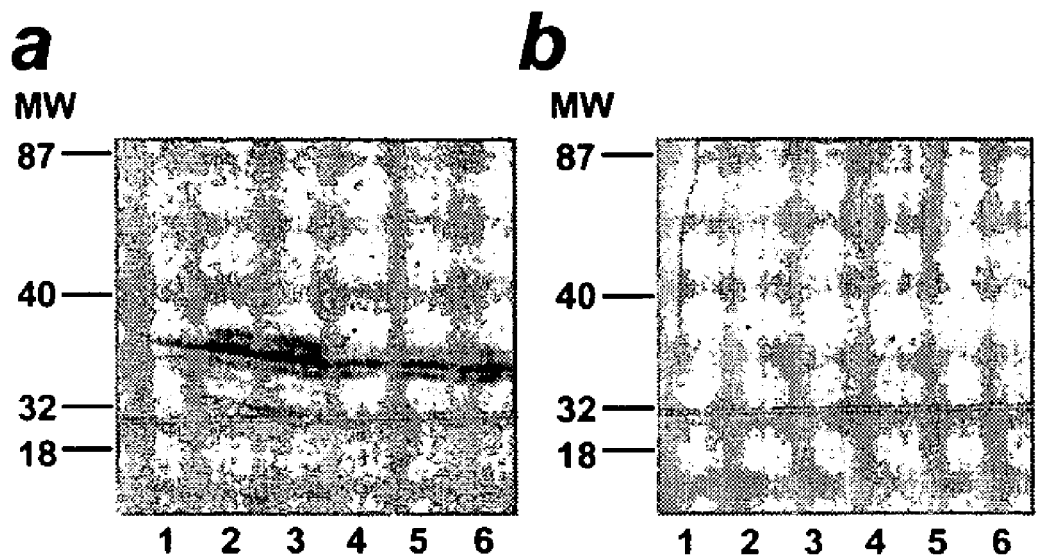

Effect of JF081204{5C} on the Incorporation of [$^3$H]-palmitate Into Platelet Intracellular Proteins The incorporation of [$^3$H]-palmitate into platelet intracellular proteins was examined to determine the effect of JF081204{5C} on platelet protein palmitoylation. Autoradiography of the membrane demonstrated several distinct bands corresponding to [$^3$H]-palmitate-labeled proteins (FIG. 14). Exposure of platelets to either 20 µM or 200 µM SFLLRN increased the intensity of the labeling. Incubation of platelets with 100 µM of JF081204 {5C} inhibited the increase in [$^3$H]-palmitate incorporation induced by either 20 µM or 200 µM SFLLRN. Staining of the Western blot membrane by Ponceau S for total protein of platelet lysates demonstrated that the major palmitoylated proteins did not correspond to major protein bands. This result indicates that certain platelet proteins are specifically palmitoylated under the conditions of this assay (FIG. 14). These data demonstrate that platelet activation influences protein palmitoylation and that JF081204{5C} interferes with platelet protein palmitoylation.

Analysis of Platelet Accrual at Sites of Vascular Injury Using Videomicroscopy

Using quantitative fluorescence videomicroscopy, the effect of the inhibition of the palmitoylation cycle on platelet accumulation at arterial injury sites was directly observed in real time. The infusion of JF081204 {5C} significantly inhibited the accumulation of platelets into a growing thrombus in the microvasculature of a living mouse in comparison to thrombus formed before the infusion (FIG. 15a). The anti-thrombotic effect on the maximum platelet accumulation and stabilized platelet accumulation after laser injury by inhibiting the palmitoylation cycle was examined (n=28 to 36). The maximum platelet accumulation was measured by determining the value representing the highest total fluorescence observed for each thrombus. JF081204{5C} inhibited maximum platelet accumulation in a dose-dependent manner by up to 80% (FIG. 15b). The stabilized platelet accumulation when thrombus size remained constant was determined by measuring the fluorescence 5 minutes following laser injury. The compound inhibited stabilized platelet accumulation in a dose-dependent manner by up to 75% (FIG. 15c). These results show that inhibition of the palmitoylation cycle by JF081204{5C} controls the in vivo accumulation of platelets at sites of arterial injury.

To understand the effect of palmitoylation on the kinetics of platelet accumulation into thrombi, the accumulation of platelets was analyzed over time, following arteriolar injury. In this mouse model, platelet accumulation following laser-induced endothelial cell injury occurs in a specific temporal pattern in which the amount of platelet accumulation varies over time. Using the time course data recorded for thrombi in each group, a composite kinetic profile was generated based on the median platelet accumulation at 300 time points of 28 to 36 thrombi (FIG. 16a). In the absence of JF081204{5C}, three distinct phases of platelet accumulation following laser-induced endothelial injury could be observed. In the net positive phase immediately following laser injury, platelets accrue in growing thrombi for approximately 80 seconds until maximum platelet accumulation is achieved. The subsequent net negative phase is characterized by a net loss of platelets from thrombi. Following the net negative phase, platelet content in thrombi is stabilized during the constant phase. When mice were infused with 1 mg/kg, 3 mg/kg, and 6 mg/kg of JF181204{5C}, platelet accumulation was observed to be inhibited at all stages of thrombus formation (FIG. 16a). Besides reducing the amount of platelet accumulation following endothelial injury, the inhibition of the palmitoylation cycle also disrupted the temporal pattern of the three phases in the developing thrombi. In the presence of 1 mg/kg (P<0.001), 3 mg/kg (P<0.05) and 6 mg/kg (P<0.001) of JF081204{5C}, a statistically significant delay in time for thrombus to achieve 50% maximum platelet accumulation was observed These data demonstrate that the palmitoylation cycle directly controls the amount of platelet accumulation as well as the kinetics of the onset of thrombus formation. Thus, palmitoylation is a novel target for the identification of agents for the inhibition of platelet activation, platelet aggregation and thrombus formation.

OTHER EMBODIMENTS

It will be appreciated by those of skill in the art that the techniques and embodiments disclosed herein are preferred embodiments only, and that in general, numerous equivalent methods and techniques may be employed to achieve the same result.

All of the references identified hereinabove are hereby expressly incorporated herein by reference to the extent that they describe, set forth, provide a basis for or enable compositions and/or methods which may be important to the practice of one or more embodiments of the present inventions.

TABLE I $IC_{50}$s of inhibition of platelet granule secretion induced with SFLLR, U-46619, ADP, or PMA by various inhibitors (µM).

|  | SFLLR | U-46619 | ADP | PMA |
| --- | --- | --- | --- | --- |
| 9-methylene-4-(alkyl)-2,3,4,9-tetrahydro-1H-cyclopenta(b)quinoline | 5 | 400 | 650 | 300 |
| (1-methyl-1-indol-3-ylmethylene)-hydrazine carboxamine | 50 | 20 | 1000 | 1000 |
| acetic acid 3-(2,4-dichlorophenyl)-3-oxo-1-trichloromethyl-propyl ester | 50 | 20 | 200 | 200 |

TABLE I-continued

IC$_{50}$s of inhibition of platelet granule secretion induced with SFLLR, U-46619, ADP, or PMA by various inhibitors (μM).

| | SFLLR | U-46619 | ADP | PMA |
|---|---|---|---|---|
| 6-Aryl-4,5-dihydro-3(2H)-pyridazinone | 0.3 | 0.3 | 8 | >1000 |
| 1-(2-hydroxy-1,3-dioxo-indan-2-yl)-2-oxo-cyclopentanecarboxylic acid ethyl ester | 50 | 30 | 50 | >1000 |
| [1,10]Phenanthroline-5-ylamine | 50 | 30 | 100 | >1000 |
| 1-H-phenothiazine, 10-(4-morpholinylacetyl)-2-(trifluoromethyl) | 80 | 100 | 150 | 85 |
| 2-(4-Oxo-cyclohexa-2,5-dienylideneamino)-isoindole-1,3-dione | 100 | 50 | 100 | 100 |
| 5-furan-2-ylmethylene-1-naphthalen-1-yl-pyrimidine-2,4,6-trione | 100 | 50 | 60 | 150 |

TABLE II

IC$_{50}$s of inhibition of platelet GPIIbIIIa activation induced with SFLLR by various inhibitors.

| | SFLLR |
|---|---|
| 6-Aryl-4,5-dihydro-3(2H)-pyridazinone | <1 |
| 9-methylene-4-(alkyl)-2,3,4,9-tetrahydro-1H-cyclopenta(b)quinoline | 5 |
| acetic acid 3-(2,4-dichlorophenyl)-3-oxo-1-trichloromethyl-propyl ester | 30 |
| 1-(2-hydroxy-1,3-dioxo-indan-2-yl)-2-oxo-cyclopentanecarboxylic acid ethyl ester | 50 |
| [1,10]Phenanthroline-5-ylamine | 50 |
| (1-methyl-1-indol-3-ylmethylene)-hydrazine carboxamine | 50 |
| 10H-phenothiazine, 10-(4-morpholinylacetyl)-2-(trifluoromethyl) | 50 |
| 2-(4-Oxo-cyclohexa-2,5-dienylideneamino)-isoindole-1,3-dione | 100 |
| 5-furan-2-ylmethylene-1-naphthalen-1-yl-pyrimidine-2,4,6-trione | 100 |

TABLE III

Augmentation of PGE1-induced cAMP levels in platelets by various inhibitors.

| | PGE$_1$ |
|---|---|
| 9-methylene-4-(alkyl)-2,3,4,9-tetrahydro-1H-cyclopenta(b)quinoline | NA at <200 μM |
| (1-methyl-1-indol-3-ylmethylene)-hydrazine carboxamine | +at 100 μM |
| acetic acid 3-(2,4-dichlorophenyl)-3-oxo-1-trichloromethyl-propyl ester | +at 100 μM |
| 6-Aryl-4,5-dihydro-3(2H)-pyridazinone | +at 100 μM |
| 1-(2-hydroxy-1,3-dioxo-indan-2-yl)-2-oxo-cyclopentanecarboxylic acid ethyl ester | NA at 1 mM |
| [1,10]Phenanthroline-5-ylamine | NA at 1 mM |
| 10H-phenothiazine, 10-(4-morpholinylacetyl)-2-(trifluoromethyl) | NA at 100 μM |
| 2-(4-Oxo-cyclohexa-2,5-dienylideneamino)-isoindole-1,3-dione | NA at 1 mM |
| 5-furan-2-ylmethylene-1-naphthalen-1-yl-pyrimidine-2,4,6-trione | NA at 1 mM |

TABLE IV

Correlation between stabilized platelet accumulation and maximum platelet accumulation.

| Pyridazinone Compound | n | Median Stabilized/Maximum | $r_s$ | P-value |
|---|---|---|---|---|
| 0 mg/kg | 32 | 33% | 0.88 | <0.0005 |
| 0.3 mg/kg | 38 | 36% | 0.89 | <0.0005 |
| 0.6 mg/kg | 46 | 41% | 0.93 | <0.0005 |
| 1.2 mg/kg | 29 | 33% | 0.98 | <0.0005 | using Spearman's rank correlation

TABLE V

JF081204{5C} was tested for its ability to inhibit SFLLRN-, U46619-, A23187-, PMA-, collagen I-, and epinephrine-induced platelet α-granule secretion. In these assays, platelets were incubated with increasing doses of compound for 30 minutes. The platelets were then exposed to a maximally stimulatory dose of the indicated agonist. P-selectin surface expression was analyzed by flow cytometry using phycoerytbrin-anti-P-selectin to monitor for α-granule secretion. Platelet aggregation was measured using an aggregometer. The IC$_{50}$s for the ability of compound to inhibit platelet activation induced by the indicated agonist is shown. The potency of this compound in inhibiting SFLLRN- and epinephrine-induced activation was at least 100-fold greater than that of U46619-, PMA-, and collagen-induced activation.

| JF081204{5C} | | IC50(μm) | | | |
|---|---|---|---|---|---|
| P-Selectin Expression Induced by: | SFLLRN | 2 | Platelet Aggregation Induced by: | SFLLRN | 2 |
| | U-46619 | 400 | | U46619 | 400 |
| | A23187 | >300 | | Epinephrine | 5 |
| | PMA | 300 | | Collagen | >200 |

What is claimed is:

1. A method of reducing platelet activation, platelet aggregation or thrombosis in a patient, comprising administering to said patient in need thereof an effective amount of a compound selected from the group consisting of

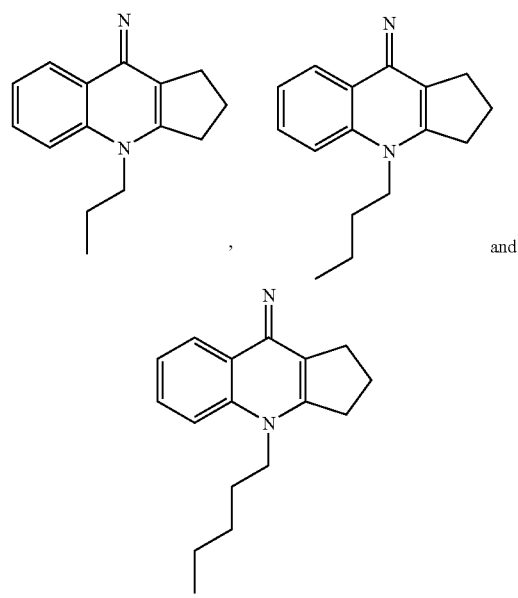

or pharmaceutically acceptable salt to reduce the platelet activation, platelet aggregation or thrombosis.

* * * * *